(12) United States Patent
Kim

(10) Patent No.: US 7,037,715 B2
(45) Date of Patent: May 2, 2006

(54) MULTIMERIZED DBH ENHANCER DOMAINS

(75) Inventor: Kwang-Soo Kim, Lexington, MA (US)

(73) Assignee: The McLean Hospital, Belmont, MA (US)

( * ) Notice: Subject to any disclaimer, the term of this patent is extended or adjusted under 35 U.S.C. 154(b) by 66 days.

(21) Appl. No.: 10/350,257

(22) Filed: Jan. 23, 2003

(65) Prior Publication Data

US 2004/0024191 A1 Feb. 5, 2004

Related U.S. Application Data

(63) Continuation of application No. 09/688,748, filed on Oct. 16, 2000, now Pat. No. 6,525,189.

(60) Provisional application No. 60/159,695, filed on Oct. 15, 1999.

(51) Int. Cl.
*C12N 15/00* (2006.01)
(52) U.S. Cl. .................................. 435/320.1; 536/24.1
(58) Field of Classification Search .............. 536/24.1; 435/320.1
See application file for complete search history.

(56) References Cited

U.S. PATENT DOCUMENTS 5,665,567 A 9/1997 Eichner et al.

FOREIGN PATENT DOCUMENTS

WO    WO 90/01550    2/1990

OTHER PUBLICATIONS

Afar et al., Positive and negative elements contribute to the cell-specific expression of the rat dopamine beta-hydroxylase gene, Brain Res. Mol. Brain Res., 36: 79-92, (1996).
Hoyle et al., Cell-specific expression from the human dopamine beta-hydroxylase promoter in transgenic mice is controlled via a combination of positive and negative regulatory elements, J. Neurosci., 14:2455-2463, (1994).
Ishiguro et al., Identification of a negative regulatory element in the 5'-flanking region of the human dopamine beta-hydroxylase gene, Brain Res. Mol. Brain Res., 34: 251-261, (1995).
Ishiguro et al., Neuron-specific expression of the human dopamine beta-hydroxylase gene requires both the cAMP-response element and a silencer region, J. Biol. Chem., 268: 17987-17994, (1993).
Kim et al., The cell-specific silencer region of the human dopamine beta-hydroxylase gene contains several negative regulatory elements, J. Neurochem., 71: 41-50, (1998).
Kim et al., The cAMP-dependent protein kinase regulates transcription of the dopamine beta-hydroxylase gene, J. Neurosci., 14: 7200-7207, (1994).
Kobayashi et al., Functional and high level expression of human dopamine beta-hydroxylase in transgenic mice, J. Biol. Chem., 269: 29725-29731, (1994).
Kobayashi et al., Human dopamine beta-hydroxylase gene: two mRNA types having different 3'-terminal regions are produced through alternative polyadenylation, Nucleic Acid Res., 17:1089-1102, (1989).
Morita et al., The 5'-flanking region of the human dopamine beta-hydroxylase gene promotes neuron subtype-specific gene expression in the central nervous system of transgenic mice, Brain Res. Mol. Brain Res., 17: 239-244, (1993).
Sabban et al., Multiple pathways in regulation of dopamine beta-hydroxylase, Adv. Pharmacol., 42: 53-56, (1998).
Seo et al., Multiple protein factors interact with the cis-regulatory elements of the proximal promoter in a cell-specific manner and regulate transcription of the dopamine beta-hydroxylase gene, J. Neurosci., 16: 4102-4112, (1996).
Shaskus et al., A negative regulatory element in the rat dopamine beta-hydroxylase gene contributes to the cell type specificity of expression, J. Neurochem., 64: 52-60, (1995).
Yang et al., Paired-like homeodomain proteins, Phox2a and Phox2b, are responsible for noradrenergic cell-specific transcription of the dopamine β-hydroxylase gene, J. Neurochem., 71: 1813-1826, (1998).

(Continued)

*Primary Examiner*—James Ketter
*Assistant Examiner*—Konstantina Katcheves
(74) *Attorney, Agent, or Firm*—Clark & Elbing LLP

(57) ABSTRACT

The invention features an enhancer cassette having the formula $[X-Y]_n$, wherein each X is independently a noradrenergic cell-specific enhancer derived from a DBH gene; Y is absent or is a mono or polynucleotide that has between one and thirty nucleotides; and n is an integer between three and twenty, inclusive.

9 Claims, 16 Drawing Sheets

OTHER PUBLICATIONS

Kim et al., A previously undescribed intron and extensive 5' upstream sequence, but not Phox2a-mediated transactivation, are necessary for high level cell type-specific expression of the human norepinephrine transporter gene, J. Biol. Chem., 274: 6507-6518, (1999).

Pattyn et al., The homeobox gene Phox2B is essential for the development of autonomic neural crest derivatives, Nature, 399: 366-370, (1999).

Stanke et al., The Phox2 homeodomain proteins are sufficient to promote the development of sympathetic neurons, Development, 126: 4087-4094, (1999).

Kim et al., Noradrenergic-specific transcription of the dopamine β-hydroxylase gene requires synergy of multiple cis-acting elements including at least two Phox2a-binding sites, J. Neurosci., 18: 8247-8260, (1998).

Kim et al., Identification and functional characterization of cell-specific and general cis-regulatory elements residing in the 5' proximal region of the human dopamine α-hydroxylase (D.B.H.) gene, Soc. of Neuroscience Abstracts, 23: 352, (1997).

Kim et al., Paired-like homeodomain protein, Phox2a, makes multiple contacts on the 5' promoter and critically controls dopamine β-hydroxylase (DBH) gene transcription, Soc. of Neuroscience Abstracts, 24: 1265, (1998).

Swanson et al., The homeodomain protein Arix interacts synergistically with cyclic AMP to regulate expression of neurotransmitter biosynthetic genes, J. Biol. Chem., 272: 27382-27392, (1997).

Seo et al., A direct role of the homeodomain proteins Phox2a/2b in noradrenaline neurotransmitter identity determination, J. Neurochem., 80: 905-916, (2002).

Ishiguro et al, "Identification and characterization of a novel phorbol ester-responsive DNA sequence in the 5'-flanking region of the human dopamine β-hydroxylase gene," *J. Biol. Chem.* 273:21941-21949 (1998).

Genbank accession No. X13257.

```
PBS1        -171 GTGTCATTAGTGCCAATTAGAG -150    SEQ ID NO: 1
                     ****    ****
                     |   |   ||||
                             ****
Domain II    -87 CCGCTAGACAAATGTGATTACC  -66    SEQ ID NO: 2

II-m1            ..TA.................           SEQ ID NO: 33

II-m2            .......CTA............          SEQ ID NO: 34

II-m3            ............CT........          SEQ ID NO: 35

II-m4            .................GC...          SEQ ID NO: 36
```

Domain IIx8-LacZ

NSE-LacZ

1.15DBH-LacZ

FIG. 7B-LC
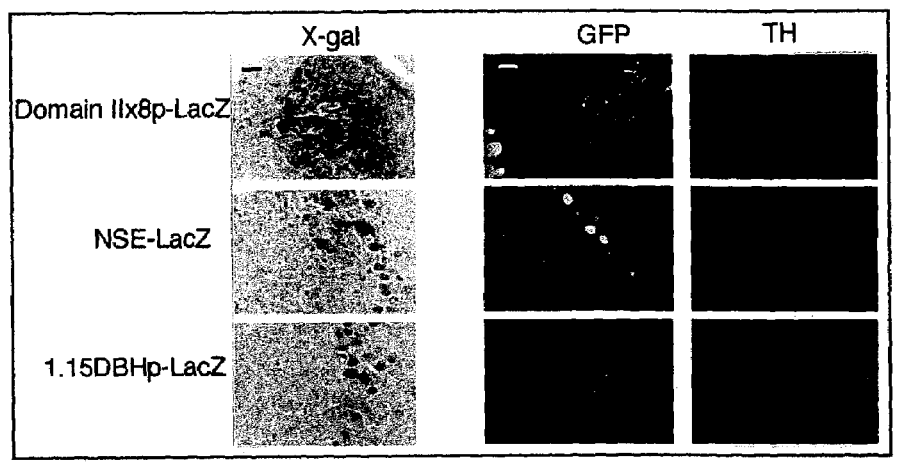
FIG. 7B-Cerebellum
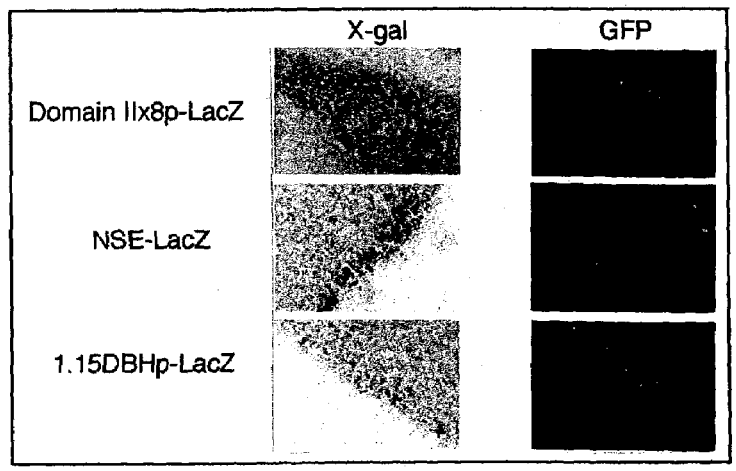
FIG. 7B-Dentate gyrus
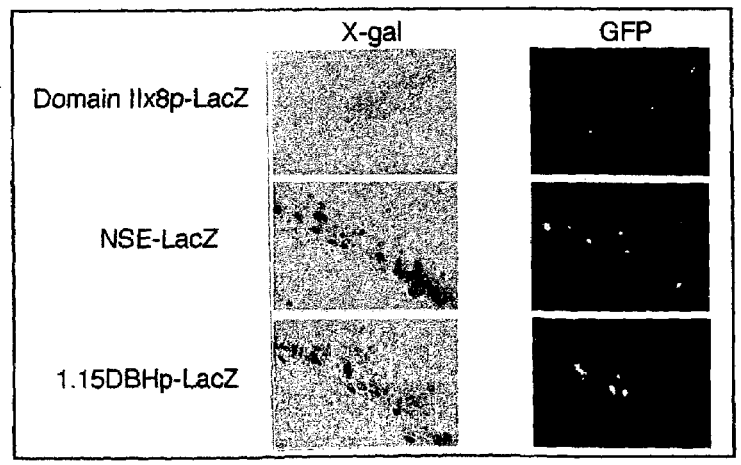

MULTIMERIZED DBH ENHANCER DOMAINS

CROSS-REFERENCE TO RELATED APPLICATIONS

This application is a continuation of U.S. patent application Ser. No. 09/688,748 (filed Oct. 16, 2000) now U.S. Pat. No. 6,525,189, which claims benefit from U.S. provisional patent application No. 60/159,695 (filed Oct. 15, 1999), each of which is hereby incorporated by reference.

STATEMENT AS TO FEDERALLY SPONSORED RESEARCH

This invention was sponsored in part by Grant #RO1-MH48866 from the National Institutes of Health. The Government has certain rights to this invention.

BACKGROUND OF THE INVENTION

The invention relates to the field of cell type-specific gene expression. Dopamine β-hydroxylase (DBH) is a hallmark protein of noradrenergic neurons because noradrenaline is synthesized by this enzyme. The highly restricted pattern of DBH expression in the nervous system predicts that this gene is subject to neuron-specific as well as to cell type-specific control mechanisms. Transgenic mice experiments have shown that 5.8 or 4 kb of the 5' flanking sequences of the human DBH gene can drive expression of the reporter gene in neurons of the locus coeruleus as well as other noradrenergic neurons and adrenal chromaffin cells, albeit with some ectopic expression. More recently, comparison of reporter gene expression in transgenic animals generated by using DBH 5' flanking regions of different lengths indicated that the upstream region between −1.1 and −0.6 kb is necessary for expression in adult and fetal noradrenergic neurons. Using cell culture systems, we and others have demonstrated that the 5' upstream region of the DBH gene can drive reporter gene expression in a cell-specific manner.

Deletional and site-directed mutational analyses have indicated that as little as 486 bp of the upstream sequence of the human DBH gene can direct expression of a reporter gene in a cell type-specific manner. In the 486 bp region of the human DBH gene, the distal part spanning −486 to −263 bp appears to have a cell-specific silencer function that contributed to suppression of the promoter activity in non-neuronal cells. Transient transfection assays identified the proximal part spanning −262 to +1 bp as sufficient and essential for the high-level DBH promoter activity in DBH-positive cells. In this 262 bp proximal area, four protein-binding regions (domains I to IV) have been identified by DNase I footprinting analysis. A cAMP response element (CRE), 5'-TGACGTCC-3' (SEQ ID NO: 3), with a single base deviation from the consensus octamer motif, 5'-TGACGTCA-3' (SEQ ID NO: 4), was shown to be critical for both the basal and cAMP-inducible transcription in DBH-expressing cell lines. This CRE is included in a composite enhancer domain structure located at −185 to −150 bp, designated domain IV, which contains several additional cis-elements such as AP1, YY1, and two core motifs of homeodomain (HD) binding sites. Site-directed mutagenesis of each sequence motif has revealed that the CRE is essential for basal promoter activity in every cell line, YY1 is multifunctional, and the AP1-like motif may be transcriptionally inactive.

The murine paired-like HD protein, Phox2a, is selectively expressed in noradrenergic cells and is critical for development of several noradrenergic neuron populations, including the locus coeruleus. The forced expression of Phox2a robustly activates DBH promoter activity, strongly suggesting a mechanism for noradrenergic-specific promoter function. Moreover, Phox2b, which contains an HD identical to that of Phox2a, has been identified and shown to be widely coexpressed with Phox2a in both the central and peripheral nervous system. Cotransfection assays showed that Phox2a and Phox2b transactivate the DBH promoter activity with a comparable efficiency.

SUMMARY OF THE INVENTION

We have discovered that an expression construct that included multiple copies of noradrenergic-specific enhancer domains isolated from the DBH gene increased the minimal promoter activity by 100- to 200-fold in DBH-positive cell lines. Moreover, we discovered that this expression construct maintained the cell-type specificity exhibited by the natural DBH promoter.

Accordingly, the invention features an enhancer cassette having the formula $[X-Y]_n$, wherein each X is independently a noradrenergic cell-specific enhancer derived from a DBH gene; Y is absent or is a mono or polynucleotide that has between one and thirty nucleotides; and n is an integer between three and fifty, inclusive. Preferably, the noradrenergic cell-specific enhancer binds specifically to Phox 2a, Phox2b, or both. Also preferably, X is independently selected from the group consisting of 5'-GTGTCATTAGTGCCAATTAGAG-3' (SEQ ID NO: 1), 5'-CCGCTAGACAAATGTGATTACC-3' (SEQ ID NO: 2), 5'-GAGGGAAAATTGGATTCCCCG-3' (SEQ ID NO: 6), 5'-GAGGGAAAATTGGATTACCCG-3' (SEQ ID NO: 8), 5'-CCGCTAGACTAATGTGATTACC-3' (SEQ ID NO: 39), 5'-GAGGGATAATTGGATTCCCCG-3' (SEQ ID NO: 40), and 5'-GAGGGATAATTGGATTACCCG-3' (SEQ ID NO: 41); Y is absent or is a mono or polynucleotide that has between one and six nucleotides; and n is between three and twenty, inclusive. In other embodiments, X includes a region that shares greater than 70% sequence identity with SEQ ID NO: 1, SEQ ID NO: 2, or SEQ ID NO: 6 and binds to Phox2a or Phox2b.

The enhancer cassette is useful for expressing a nucleic acid molecule in a noradrenergic cell. To this end, the enhancer cassette can be combined with an RNA polymerase binding site and a transcription initiation site to form an expression construct. Additionally, the enhancer cassette and expression construct of the invention can each be a component of an expression vector, such as an adenoviral vector.

As used herein, by "nucleic acid" is meant either DNA or RNA. A "nucleic acid molecule" may be a single-stranded or double-stranded polymer of deoxyribonucleotide or ribonucleotide bases. Unless otherwise specified, the left hand direction of the sequence of a single-stranded nucleic acid molecule is the 5' end, and the left hand direction of double-stranded nucleic molecule is referred to as the 5' direction.

By "promoter" is meant a region of nucleic acid, upstream from a translational start codon, which is involved in recognition and binding of RNA polymerase and other proteins to initiate transcription. A "DBH promoter" is one derived from the promoter region of a DBH gene and that, when operably linked to a heterologous nucleic acid molecule, is capable of initiating transcription of that molecule when present in a transcription medium capable of supporting transcription.

Exemplary transcription media include, for example, a mammalian cell (e.g., an immortalized cell), and a yeast cell. Also included are in vitro expression systems such as reconstituted expression medium composed of components required to support transcription, as are known in the art.

By "enhancer domain" or "domain" is meant a nucleic acid sequence that, when positioned proximate to a promoter and present in a transcription medium capable of supporting transcription, confers increased transcription activity relative to the transcription activity resulting from the promoter in the absence of the enhancer domain. By "enhancer cassette" is meant a nucleic acid sequence that includes an enhancer domain and, optionally, additional sequence that does not enhance transcription (e.g., spacer sequence).

By "multimerized enhancer domain" is meant two or more copies of a noradrenergic cell-specific enhancer domain derived from a DBH gene. Preferably, the number of copies is between three and twenty, inclusive. The enhancer domains can be in the same or opposite orientation, and can be contiguous or noncontiguous. In expression constructs having two different enhancer domains (e.g., domain A and domain B), the orientation and the 5' to 3' order (e.g., 5'-AABB-3' vs. 5'-ABAB-3') are not limitations to the invention.

By "operably linked" is meant that a nucleic acid molecule to be transcribed and an expression construct (i.e., a promoter and an enhancer domain) are connected in such a way as to permit transcription of the nucleic acid molecule in a suitable transcription medium.

By "derived from" is meant that a the nucleic acid molecule was either made or designed from a second nucleic acid molecule, the derivative retaining important functional features of the nucleic acid molecule from which it was made or designed. In the case of enhancer domains, the important features are specific binding to Phox2a and/or Phox2b and conferral of noradrenergic cell-specific expression when operably linked to a promoter. Optimization of binding and/or cell-specific expression may be performed.

By "expression construct" is meant a nucleic acid molecule that is capable of directing transcription. An expression construct of the present invention includes, at the least, a multimerized DBH enhancer domain and a promoter. Additional domains, such as a transcription termination signal, may also be included, as described herein.

By "vector" or "expression vector" is meant an expression system (e.g., an adenoviral expression system), a nucleic acid-based shuttle vehicle, a nucleic acid molecule adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "plasmid" is meant an autonomous DNA molecule capable of replication in a cell, and includes both expression and nonexpression types.

By "heterologous" is meant that the nucleic acid molecule originates from a foreign source or, if from the same source, is modified from its original form. Thus, a "heterologous promoter" is a promoter not normally associated with the multimerized enhancer domain of the present invention. Similarly, a heterologous nucleic acid molecule that is modified from its original form or is from a source different from the source from which the promoter to which it is operably linked was derived.

By "transgene" is meant any piece of a nucleic acid molecule (for example, DNA) that is inserted by artifice into a cell, and becomes part of the organism (integrated into the genome or maintained extrachromosomally) that develops from that cell. Such a transgene may include a gene that is partly or entirely heterologous (i.e., foreign) to the transgenic organism, or may represent a gene homologous to an endogenous gene of the organism.

Other features and advantages of the invention will be apparent from the following description of the preferred embodiments thereof.

BRIEF DESCRIPTION OF THE DRAWINGS

FIG. 7B is a series of photographs showing expression of lacZ following infection with the adenoviral vectors of FIG. 7A. Adenoviruses were unilaterally injected into the locus caeruleus, cerebellum, and dentate gyrus. β-galactosidase expression after four days was examined by X-gal staining. GFP expression was examined to confirm the delivery of viruses to the targeted area.

DETAILED DESCRIPTION OF THE INVENTION

Figures 1A, 1B:
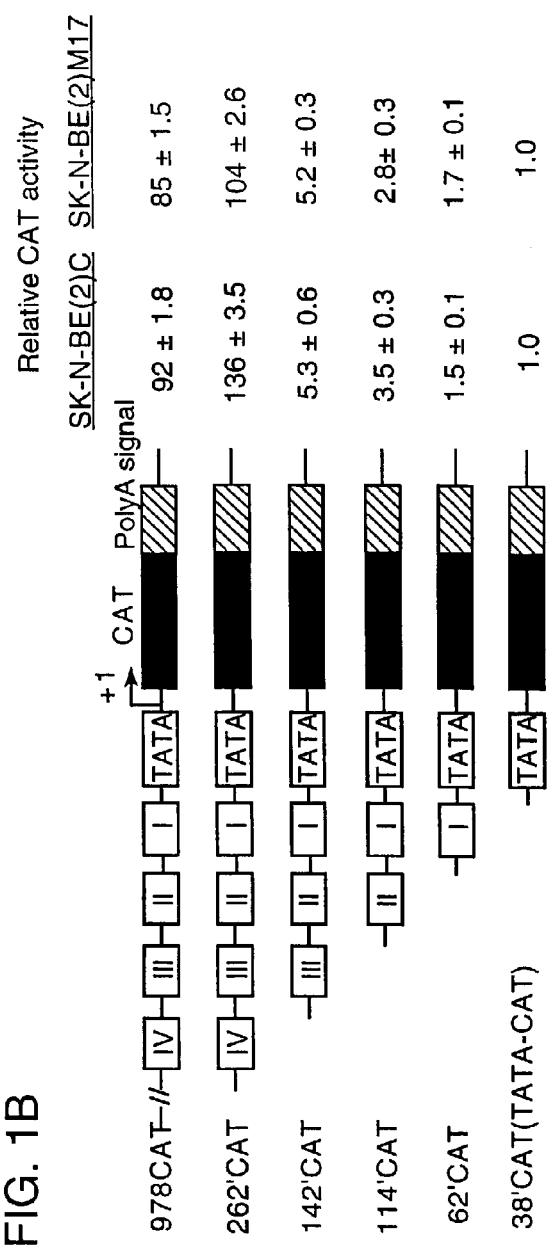
FIG. 1A is a schematic illustration showing the nucleotide sequences and the locations of domains I, II (also referred to as PBS2), and III of the human DBH gene, as identified by DNase I footprint analysis. The Sp1-binding motif and AP2-binding motif residing in domain I and III, respectively, are indicated by brackets. Base substitutions within each domain that are analyzed by EMSA and transient transfection assays are also indicated.
FIG. 1B is a schematic illustration showing the promoter activity of deletional DBH-CAT reporter constructs, as determined by transient transfection assays in DBH-expressing SK-N-BE(2)C and SK-N-BE(2)M17 cell lines, and expressed relative to that of the minimal 38'CAT construct.

We have discovered that Phox2a interacts with the HD binding site residing within domains II and IV of the human DBH gene in a cell-specific manner and can directly control noradrenergic cell-specific DBH promoter activity. Multimerization of domain II (also referred to as PBS2) increased the promoter activity of a minimal DBH promoter by approximately 2000-fold in DBH-positive cell lines without compromising cell specificity. Cotransfection of a Phox2a-expression vector dramatically increased the activity of the multiple PBS2-promoter construct only in DBH-negative cell lines, confirming that PBS2 is responsive to Phox2a.

In vivo, an adenoviral expression vector containing the multimerized DBH enhancer domains exhibited strong expression and greater cell-specific expression than did the entire 1.1 kb DBH promoter, indicating that the duplicated enhancer domains will be useful, for example, for driving robust gene expression in noradrenergic cells in gene therapy.

We have also discovered Phox2a binding sites that can be mutated to increase expression levels in noradrenergic cells.

Multimerized DBH Enhancer Domains

In one embodiment, the invention features multimerized enhancer domains. The multimerized enhancer domains of the invention are derived from DBH genomic sequence. Taking the first nucleotide of the mRNA as position +1, noradrenergic enhancer domains are located, for example, from about −150 to −171, −66 to −87, and −87 to −105. It will be understood that the nucleotide positions can be altered by about five to ten base pairs without substantially altering the transcription-enhancing ability of an enhancer domain. The enhancer domain that is multimerized will usually be about 10 to 40 bp in length. In addition to the noradrenergic cell-specific enhancer domains described herein, the invention features enhancer domains that are variants or modifications of these enhancer domains. For example, one or more nucleotides of the enhancer domain can be altered, using standard techniques, without altering Phox2a-specific binding or noradrenergic cell-specific expression. Using techniques described herein, one can readily ascertain whether any alteration of an enhancer domain results in either altered binding or expression.

We have now discovered that the property that results in noradrenergic cell-specific expression is most likely to be binding to Phox2a and/or Phox2b. Moreover, these two transcription factors bind to both PBS2 and PBS1, even though the two domains share little sequence identity. Based on our findings, we can generate, using standard techniques such as PCR or oligonucleotide synthesis, artificial enhancer domains that specifically bind to Phox2a and/or Phox2b and increase promoter activity specifically in noradrenergic cells. Thus, any multimerized enhancer domain that specifically binds Phox2a and/or Phox2b is considered part of the invention.

Preferably, the multimerized enhancer domain is incorporated into an enhancer cassette having the formula $(X-Y)_n$, wherein X corresponds to a noradrenergic cell-specific enhancer derived from a DBH gene, Y is absent or is a mono or polynucleotide that has between one and thirty nucleotides, and n is an integer between 1 and 50 inclusive (preferably between 2 and 16). It is understood that n can be even greater than 50 (e.g., 100, 200, 500, or more). In preferred embodiments, X has a sequence selected from a group consisting of 5'-GTGTCATTAGTGCCAATTAGAG-3' (SEQ ID NO: 1), 5'-CCGCTAGACAAATGTGATTACC-3' (SEQ ID NO: 2), 5'-GAGGGAAAATTGGATTCCCCG-3' (SEQ ID NO: 6), 5'-GAGGGAAAATTGGATTACCCG-3' (SEQ ID NO: 8), 5'-CCGCTAGACTAATGTGATTACC-3' (SEQ ID NO: 39), 5'-GAGGGATAATTGGATTCCCCG-3' (SEQ ID NO: 40), and 5'-GAGGGATAATTGGATTACCCG-3' (SEQ ID NO: 41). In other embodiments, X has greater than 70% sequence identity to SEQ ID NO: 1, SEQ ID NO: 2, or SEQ ID NO: 6 and binds to Phox 2a or Phox 2b.

Although domain IV contains several cis-elements critical for DBH transcription, when placed 5' to the TATA and transcription start site, it was able to recapitulate neither intact basal level nor noradrenergic cell-specific transcription of the reporter gene. This lack of specificity is most likely due to the inclusion of the CRE, which is not cell-specific, and thus it is preferred that multimerized enhancer domains do not include CREs. Multimerized enhancer domains result in greatly increased promoter activity; either PBS2 or domain IV alone mediated Phox2a/Phox2b-induced transcription only modestly (approximately 3-fold) compared to the intact DBH promoter-enhancer region (10- to 15-fold).

Expression Constructs

In one particular embodiment of the present invention, the multimerized enhancer domains or enhancer cassettes are placed in the proximity of a promoter; together, these form an expression construct. An exemplary expression construct is shown in FIG. 6.

An enhancer domain is cis-acting and desirably is located within about 5 kb, typically about 2 kb, more typically adjacent to or within about 1 kb of a promoter to be enhanced. The combination of the multimerized enhancer domain and the promoter is considered to be an "expression construct". In the expression construct, the enhancer domains may be in either orientation with respect to each other as well as to the promoter, and can be located 5' or 3' in relation to the promoter they enhance, usually in the 5' direction.

A multimerized enhancer domain finds use with a wide variety of promoters, including promoters that are naturally found under the control of the enhancer, i.e., in a cis position (adjacent and homologous) and those not normally associated with the particular promoter (i.e., heterologous).

The promoter may be derived from the same or different kingdom, family, or species as the multimerized DBH enhancer domains. Sources of promoters include viruses, prokaryotes and eukaryotes, such as bacteria, plants, insects, and mammals.

In addition to the aforementioned multimerized enhancer domain and promoter, the expression constructs may also include regulatory control regions that are generally present in the 3' regions of human genes. For example, a 3' terminator region may be included in the expression vector to increase stability of the mRNA.

Expression Vectors

In addition to an expression construct, an expression vector typically contains a dominant selectable marker gene used to identify those cells that have become transformed. Useful selectable genes include genes encoding antibiotic resistance genes, for example, those encoding resistance to hygromycin, kanamycin, bleomycin, G418, streptomycin, or spectinomycin. Alternatively, the green-fluorescent protein from the jellyfish *Aequorea victoria* may be used as a selectable marker.

The invention also contemplates DNA constructs in which an expression construct, including a multimerized noradrenergic cell-specific enhancer domain and a promoter, is operably linked to a nucleic acid molecule one wishes to be transcribed. The nucleic acid molecule may have a natural open reading frame (ORF), as well as transcribed 5' and 3' sequences flanking the ORF. Alternatively, it may be in the "antisense" orientation in that it encodes the complement of an RNA molecule or portion thereof. When the construct includes an ORF (which encodes a polypeptide), an enhanced transcription initiation rate is obtained, usually providing an increased amount of the polypeptide. For protein production, translational initiation sequences (including a start codon) are included in the constructs, either from the promoter domain, from the attached coding sequences, or from a heterologous source. When the construct contains an antisense sequence, complementary to the wild-type molecule, decreases the amount of polypeptide product. The nucleic acid molecules of interest which are transcribed will be of at least about 8 bp, usually at least about 12 bp, more usually at least about 20 bp, and may be one kb or more in length.

Methods for Making Multimerized Enhancer Domains

A variety of multimerized DBH enhancer domains can be produced using standard molecular biology techniques. For example, a multimerized enhancer can be constructed by first mapping restriction enzyme sites in the DBH genomic sequence that includes the enhancer domain of interest, then, using the constructed map to determine the appropriate restriction enzymes, excising the domain of interest and recombining it to form a multimerized enhancer domain. Alternatively, a multimerized enhancer domain or an expression construct of the present invention can be synthesized by a variety of methods based on the sequences described herein. Synthesis can be accomplished by chemical synthesis methods for the production of enhancer oligonucleotides. In addition, a nucleic acid molecule can be prepared by the synthesis of a series of oligonucleotides which correspond to different portions of the nucleic acid molecule, and which can be combined by ligation to form larger nucleic acid molecules. Finally, oligonucleotides can be used as primers in a polymerase chain reaction (PCR) to amplify a nucleic acid molecule of interest. The primers can further contain restriction sites to facilitate ligation of the PCR fragments.

The expression constructs are typically prepared employing cloning vectors, where the sequences may be naturally occurring, mutated sequences, synthetic sequences, or combinations thereof. The cloning vectors are well known and include prokaryotic or eukaryotic replication systems, markers for selection of transformed host cells, and unique dual restriction sites for insertion or substitution of sequences.

EXAMPLE 1

Phox2a is Coexpressed with DBH and Interacts with the Putative HD-Binding Site of the Human DBH Gene in a Cell-Specific Manner Domain IV, located at −185 to −150 bp upstream of the transcription start site of the human DBH gene, contains several potential cis-regulatory elements such as the CRE, AP1, YY1, and two core motifs of HD-binding site in an overlapping composite structure. Previous studies have indicated that this region is critical for DBH transcription, and multiple protein factors may bind to this region in a cell-specific manner. To identify noradrenergic-specific DNA-protein complexes, nuclear extracts from DBH-expressing (SK-N-BE(2)C, CATH.a, and PC12) and nonexpressing (HeLa and C6 glioma) cell lines were compared by EMSA. Using radiolabeled oligonucleotide C/Y/A and domain IV as the probe, we failed to identify any DNA-protein complex that, either directly or indirectly, correlated with the noradrenergic phenotype. To determine whether any cognate protein factors interact with the HD-binding site in a noradrenergic-specific pattern, we incubated different nuclear extracts with radiolabeled oligonucleotide HD and analyzed DNA-protein complexes in EMSA. Two major complexes were formed by most nuclear extracts. Thus, both DBH-expressing and -nonexpressing cell lines appear to contain a protein factor that bound to the HD site of the DBH gene. Nuclear extracts from C6 glioma cells produced several complexes with faster mobility. The DNA-protein complexes, including those formed by C6 extracts, were competed by an excess of HD oligonucleotide, but not by other nonrelated oligonucleotides (e.g., Sp1), indicating that they represent sequence-specific complexes. To determine whether the two ATTA core motifs, designated HD1 and HD2, are important for forming these complexes, we performed competition assays using wild type or mutant oligonucleotides. HDm1, containing substitutions within HD1, competed formation of DNA-protein complexes as efficiently as did wild type HD oligonucleotide. In contrast, HDm2 was unable to compete formation of complexes, indicating that HD2, but not HD1, is critical for formation of these complexes in all these cell lines. Consistent with this, radiolabeled HDm1 produced DNA-protein complexes as robustly as the wild type, but radiolabeled HDm2 barely formed any complex.

We next tested whether Phox2a is involved in forming complexes with the HD-binding site. Supershifted bands were specifically formed with the radiolabeled wild type HD oligonucleotide when Phox2a-specific antibody (raised against the carboxy terminus of Phox2a; described in Tiveron et al., J. Neurosci. 16:7649–7660, 1996) was preincubated with nuclear extracts from DBH-expressing cell lines but not with those from DBH-negative cell lines. When nuclear extracts were preincubated with preimmune serum or antibodies against CREB or Sp1, no supershifted bands were detected. This result indicates that Phox2a is restrictively expressed in DBH-expressing cell lines, although other HD-binding proteins evidently also exist in all cell lines. The overall level of DNA-protein complex formation was not noticeably diminished even though supershifted bands were conspicuously formed. While this finding suggests that Phox2a may constitute only a small portion of protein factors that interact with the HD site, it also indicates that properties of Phox2a protein, e.g., stability or DNA-binding affinity, can be modulated by interaction with specific antibody. Using two additional Phox2a-specific antibodies that were raised against Y75-R88 of Phox2a, identical results were obtained in supershift assays.

We examined the correlated expression of DBH and Phox2a in greater detail using mRNAs prepared from five catecholaminergic (human neuroblastoma SK-N-BE(2)C and SK-N-BE(2)M17, rat pheochromocytoma PC12, and mouse CATH.a and PATH.2) and five noncatecholaminergic (human HeLa, human cholinergic neuroblastoma SK-N-MC11, rat glioma C6, human thyroid carcinoma, and mouse mastocytoma) cell lines. We found a striking correlation of DBH and Phox2a expression among all these cell lines analyzed. All three DBH-expressing cell lines appeared to produce a major Phox2a transcript of 1.7 kb, as previously reported (Valarche et al., Development, 119: 881–896, 1993). Additional Northern blot experiments with longer run of samples indicated that the human SK-N-BE(2)C and SK-N-BE(2)M17 cell lines produce a slightly bigger (2.0 kb) transcript of Phox2a, compared to the rat PC12 and mouse CATH.a and PATH.2 cell lines (1.7 kb). Interestingly, Phox2b transcript was expressed in only SK-N-BE(2)C and PC12 cell lines. All five non-catecholaminergic cell lines did not express any detectable message RNA for TH, DBH, Phox2a, or Phox2b.

EXAMPLE 2

Mutation of a Single HD Core Motif Converts the Upstream Region of the DBH Gene into a Nonspecific Enhancer To determine the role of individual cis-regulatory elements residing within domain IV in cell-specific DBH transcription, we mutagenized individual motifs in the context of the 978 bp upstream sequence of the human DBH gene, which is able to direct cell-specific transcription in the transient expression assay (Ishiguro et al., J. Biol. Chem., 268:17987–17994, 1993). Base substitutions within the CRE motif diminished most DBH promoter activity in DBH-expressing and -nonexpressing cell lines alike. This result indicates that the CRE is important for DBH promoter function regardless of the cell type. Mutation of three bases within HD2, which blocked DNA-protein interaction at the HD-binding region in EMSA, virtually abolished transcriptional activity in SK-N-BE(2)C cell line and significantly diminished transcriptional activity (60–80%) in SK-N-BE (2)M17 and CATH.a cell lines. Strikingly, the same mutation did not alter or modestly increased the transcriptional activity in DBH-negative HeLa and C6 cells. Thus, HD2 appears to be exclusively active in noradrenergic cell lines. Another HD-binding core motif, HD1, was also mutated to make the mHD1 construct. This mutation likewise diminished, albeit to a lesser degree, the transcriptional activity in all three DBH-expressing cell lines but did not alter transcriptional activity in DBH-nonexpressing cell lines. The prominent effect of HD1 mutation on DBH promoter function was rather surprising in view of EMSA results, which indicated that this mutation barely affects DNA-protein interaction at this region. Simultaneous mutation of HD1 and HD2 diminished the DBH promoter activity in SK-N-BE(2)M17 and CATH.a cells more severely. Mutation analysis did not support the YY1 and AP1-like motif as noradrenergic-specific enhancers.

EXAMPLE 3

Expression of Phox2a or Phox2b in DBH-nonexpressing Cells Transactivates the Promoter Activity of the Human DBH Gene The observations that the HD-binding site of domain IV (PBS1) is a critical cell-specific enhancer and that its cognate factors Phox2a and Phox2b are expressed only in DBH-positive cells led us to hypothesize that they play a direct role in cell-specific transcription of the DBH gene. To test this, Phox2a- and Phox2b-expressing vectors were transiently cotransfected along with the DBH-CAT reporter gene construct. Transcriptional activity of DBH978CAT was not significantly modulated by Phox2a or Phox2b in SK-N-BE (2)C cells. In contrast, expression of either Phox2a or Phox2b activated the transcriptional activity of DBH978CAT up to 10-fold in a dose-responsive manner in C6 cells. Coexpression of Phox2a and Phox2b marginally potentiated their transactivating function, indicating that they are functionally independent. We further tested the transactivating function of Phox2a and Phox2b in additional DBH-expressing and nonexpressing cell lines. In the CATH.a cells, expression of Phox2a and/or Phox2b modestly facilitated the transcriptional activity of DBH978CAT. In HeLa cells, expression of Phox2a and/or Phox2b activated the transcriptional activity of DBH978CAT up to 15-fold.

EXAMPLE 4

Transcription of the Human DBH Gene

In transient transfection assays using DBH-expressing SK-N-BE(2)C and SK-N-BE(2)M17 cell lines (FIG. 1B), deletion of domain IV resulted in a dramatic decrease (20- to 30-fold) of the transcription activity in both cell lines. Further deletion of domains III, II, and I resulted in a progressive decrease of the promoter activity, indicating that all three domains may act as positive regulators of the DBH promoter function in DBH-positive cells.

Figure 1C:
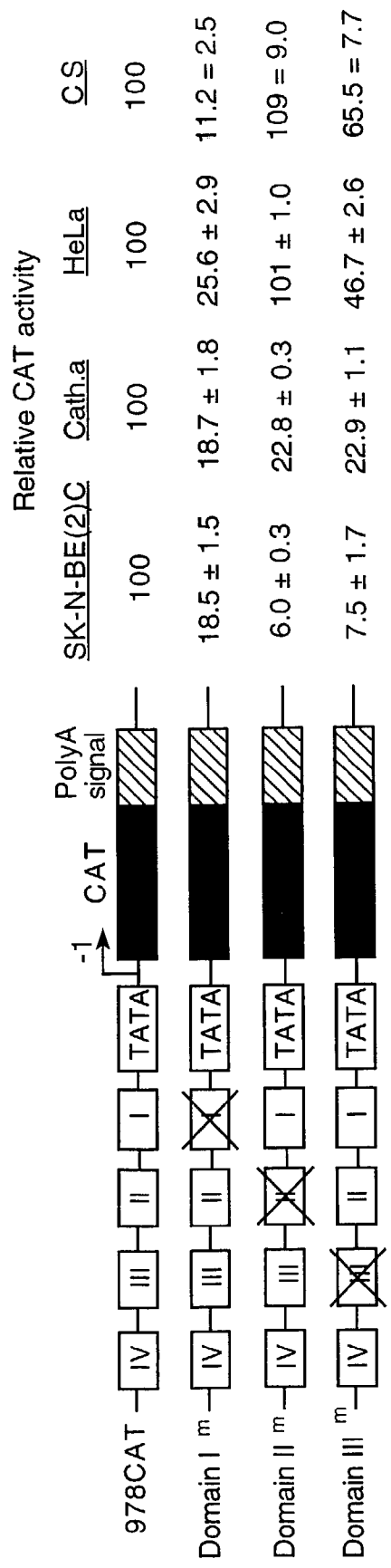
FIG. 1C is a schematic illustration showing the effect of site-directed mutation of each cis-regulatory element on DBH promoter activity in the context of the upstream 978 bp sequences in DBH-expressing (SK-N-BE(2)C and CATH.a) and nonexpressing (HeLa and C6) cell lines. The normalized CAT activity driven by 978CAT in each cell line was set to 100 to compare the effect of each mutation on cell-specific promoter function of the DBH upstream sequence. The relative values are presented as mean±SEM values from six to eight independent samples.

Base substitutions within each motif were introduced in the context of the 978 bp DBH promoter-enhancer region and examined for effects on promoter activity in both DBH-positive and -negative cells (FIG. 1C). The CAT activity driven by the intact 978 bp DBH promoter-enhancer in DBH-positive cell lines was much higher than that in DBH-negative cell lines (typically >10-fold), but was given the relative value of 100 in each cell line to compare the relative effect of individual mutation on the promoter activity. Base substitutions within domain I, II, or III diminished greater than 80% of the promoter activity in DBH-positive cells, suggesting that these proximal cis-elements activate DBH transcription in an interdependent manner. Mutation of domain I equally diminished most of DBH promoter activity in DBH-negative cells, while domain III mutation was several-fold less effective in the negative cell lines. Base substitutions in PBS2 diminished DBH promoter activity only in DBH-expressing cells, indicating that PBS2 is a critical noradrenergic cell-specific cis-acting element.

Figure 2:
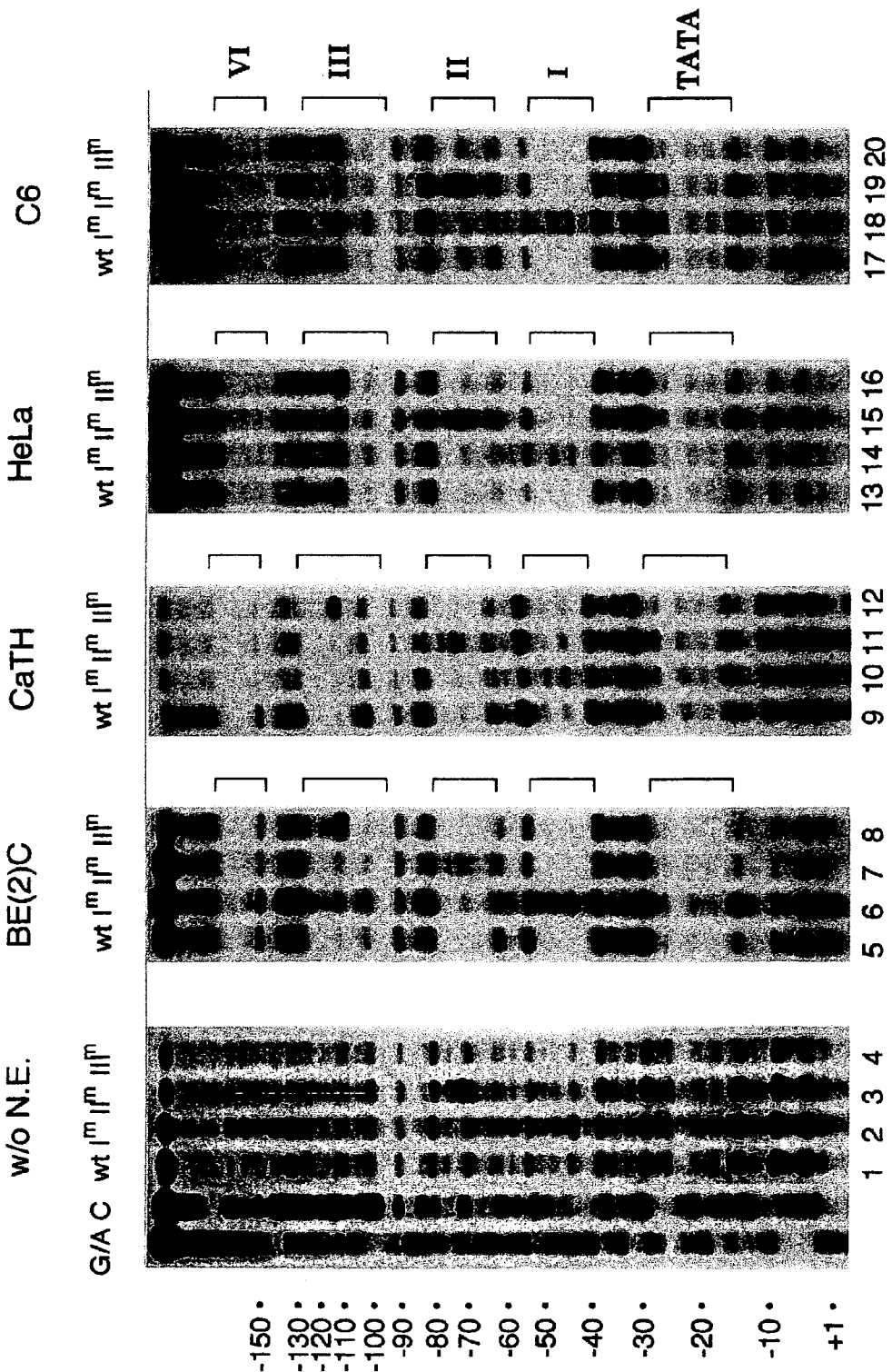
FIG. 2 is a series of photographs of autoradiographs showing nuclear extracts from SK-N-BE(2)C, CATH.a, HeLa, and C6 cells used for DNase I footprinting analyses of the wild type and mutant sequence upstream from the human DBH gene. The coding strand probes were prepared using wild type (lane 1), domain Im (lane 2), domain IIm (lane 3), and domain IIIm (lane 4) mutant constructs. Domain II is equivalent to PBS2. The TATA box and four footprinted domains are denoted by brackets at the right side of the panel.

Using different nuclear extracts, we next performed DNase I footprint analyses of the wild type and mutant promoter-enhancers (FIG. 2) to address (i) whether there is a positive correlation between promoter function and DNA-protein interaction and (ii) whether cognate nuclear factors synergistically bind to these proximal protein binding sites. We found that patterns of DNA-protein interaction appeared to be significantly different between DBH-positive and -negative cell lines. For example, a hypersensitive site at −161 bp appeared only with DBH-positive extracts. Moreover, footprinting at domains II and III was much more evident with DBH-positive extracts (FIG. 2; compare lanes 5 and 9 with 13 and 17). Mutation of each motif specifically blocked footprinting at that site, demonstrating a direct correlation between promoter function and DNA-protein interaction at each motif. Mutation of one site did not impair DNA-protein interactions at other sites, including domain IV, suggesting that the transcription factors bind to the corresponding sites independently of each other. This conclusion was further supported by additional footprinting experiments using suboptimal amounts of nuclear extracts, which protected these domains only incompletely.

EXAMPLE 5

PBS2 Interacts with Cognate Protein Factors in a Cell-specific Manner

Figure 3A:
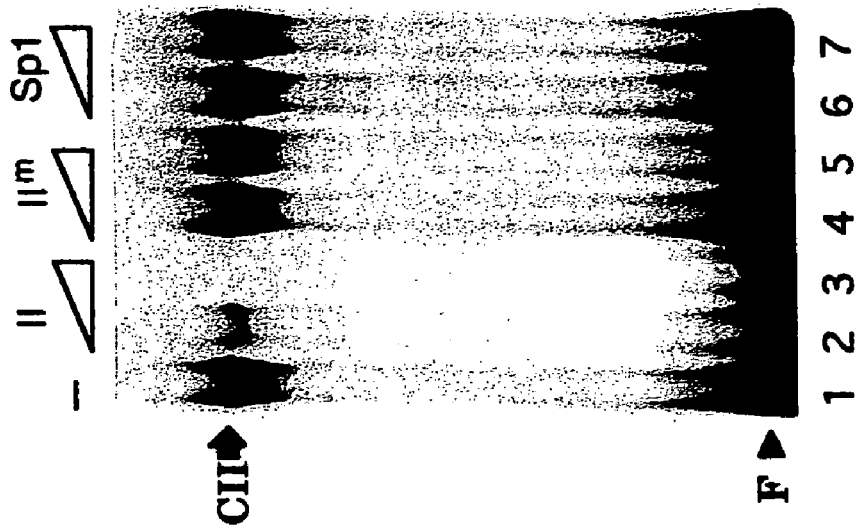
FIGS. 3A and 3B are a series of photographs of autoradiographs showing that domain II (PBS2) interacts with nuclear proteins in a cell-specific manner.
Figure 3B:
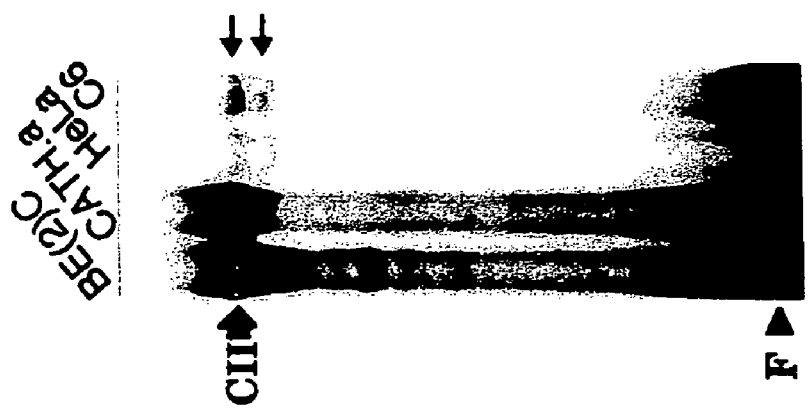
Figure 4A:
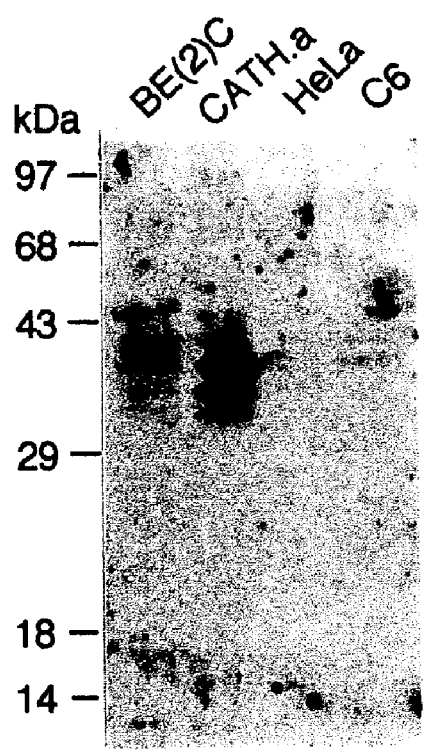
FIG. 4 is a series of photographs of autoradiographs showing the identification of noradrenergic neuron-specific protein factors that interact with domain II (PBS2) by Southwestern blot analysis.
Figure 4B:
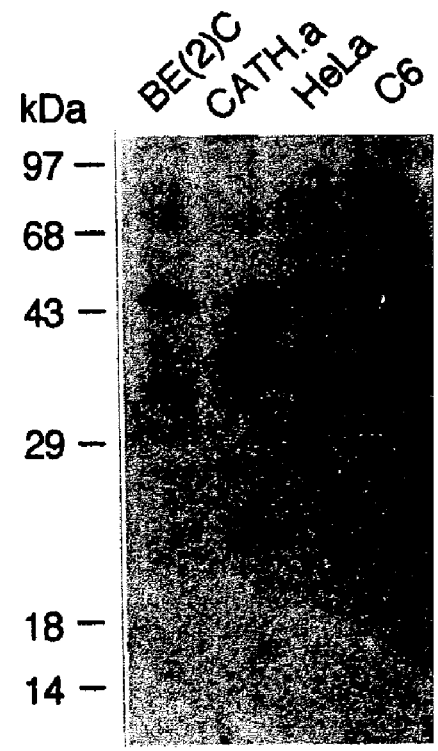

We determined, using DNase I footprint analysis, that PBS2 selectively interacts with nuclear proteins from noradrenergic cells (FIG. 2). In support of this finding, nuclear extracts from DBH-positive cells robustly formed the complex CII (FIG. 3A). In competition assays, molar excesses of cold PBS2 oligonucleotide, but not its mutant form or unrelated Sp1 oligonucleotide, abolished formation of CII, strongly suggesting that it represents a sequence-specific complex (FIG. 3B). To further test whether the cognate protein factors of PBS2 exist in a noradrenergic-specific manner, Southwestern analysis was performed using nuclear proteins prepared from DBH-positive and -negative cells (FIG. 4). This analysis demonstrated that, in DBH-positive cells, several nuclear protein factors interact with PBS2. Two protein bands of 39 and 40 kDa were detected in SK-N-BE(2)C cells, while protein bands of 38 and 35 kDa were evident in CATH.a cells (FIG. 4A). In contrast, nuclear proteins from DBH-negative cells did not show any prominent signals. In further support of sequence specific binding between PBS2 and cognate protein factors, a 100-fold molar excess of cold PBS2 oligonucleotide abolished most of the signals (FIG. 4B).

EXAMPLE 6

PBS2 is a Phox2a-binding Site

Figures 5A, 5B:
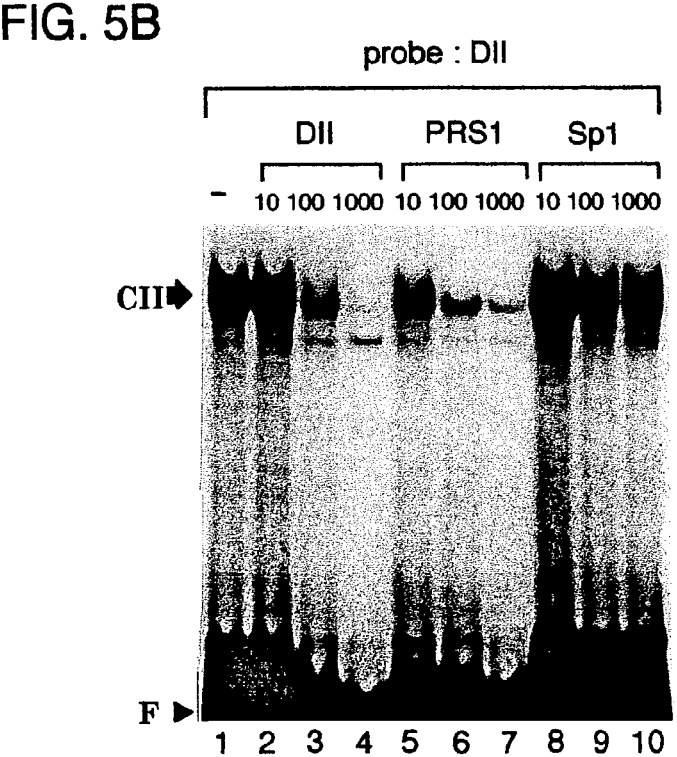
FIG. 5A is a schematic illustration showing nucleotide sequences of the HD binding site of domain IV (also referred to herein as PBS1) and wild type and mutant of domain II (PBS2) oligonucleotides. The ATTA motifs are indicated by asterisks. Mutated bases are shown in the mutant oligonucleotides. Dots represent unchanged sequences.
FIG. 5B is a photograph of an autoradiograph showing that the DNA-protein complexes formed with SK-N-BE(2)C nuclear proteins and the DII (PBS2) oligonucleotide were competed by molar excesses of different cold oligonucleotides as indicated above each panel. Thirty micrograms of nuclear proteins were used in each binding reaction.

Our findings that PBS2 binds to nuclear proteins in a cell-specific manner, and that its mutation is associated with a severe loss of DBH promoter function only in noradrenergic cells, prompted us to characterize and identify the cognate nuclear factors. The nucleotide sequence of PBS2 is A/T-rich, and our previous sequence search did not reveal significant homology to any known cis-acting motif. To determine nucleotide bases important for PBS2-protein factor interaction, we performed EMSA using PBS2 or mutant oligonucleotides containing double or triple base substitutions at different locations as probes (FIG. 5A). Mutant m1 and m2 probes containing base substitutions at the 5' side of PBS2 were able to form complexes with an efficiency comparable to that of the wild type PBS2 oligonucleotide with nuclear proteins prepared from SK-N-BE(2)C (lanes 1–3, FIG. 5D) or CATH.a cells. In contrast, m3 and m4 probes no longer generated signals as prominent as the wild type sequence (lanes 4–5, FIG. 5D), indicating that nucleotides residing at the 3' side are critical for PBS2-protein interactions. The m4 probe, showing the most severe defect in forming the DNA-protein complex, has base substitutions within the ATTA motif of the HD-binding site at the 3' side, raising the possibility that PBS2 may represent, in addition to the PBS1 within domain IV, a second Phox2a/Phox2b-binding site. To test this, we further analyzed DNA-protein interaction at PBS2 using competition and supershift assays. Using the DII (PBS2) oligonucleotide as the probe, the cold PBS1 oligonucleotide was able to compete formation of DNA-protein complexes even more efficiently than the cold DII (PBS2) oligonucleotide (lanes 1 to 10, FIG. 5B). These competition assays indicate that common nuclear factors interact with domain IV and, with a lower affinity, with PBS2. The lower affinity exhibited by PBS2 is presumably due to the fact that PBS1 contains two ATTA core motifs, while PBS2 has only one such motif.

Figures 1, 5C:
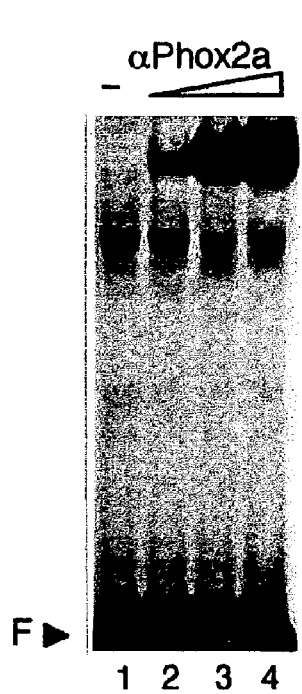
FIG. 5C is a series of photographs of autoradiographs showing antibody supershift assays that indicate that Phox2a binds to both domain II (PBS2) (SEQ ID NO: 2) and PRS1 (PBS 1) (SEQ ID NO: 1). Coincubation of nuclear proteins with increasing amounts of 1 μL of $10^{-2}$ (lanes 2 and 6), $10^{-1}$ (lanes 3 and 7) and 1:3 dilution (lanes 4 and 8) of Phox2a-specific antibody resulted in the generation of a supershifted band (indicated by an arrowhead) in a dose-responsive manner with both PBS1 (left panel) and DII (PBS2) oligonucleotide (right panel). Coincubation with either SP1 or AP2-specific antibody (0.1 μg each) neither generated the supershifted band nor diminished formation of CII (lanes 9 and 10).
Figures 2, 5C:
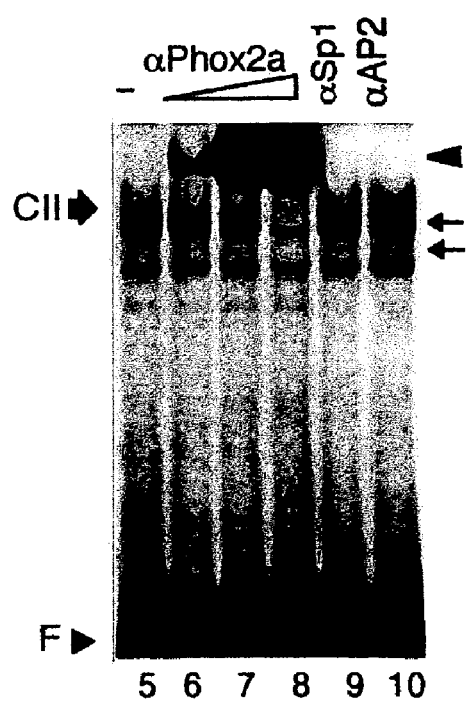

To address whether PBS2-protein complexes contain Phox2a, a supershift assay was performed using Phox2a-specific antibody. In a control experiment using radiolabeled PBS1 oligonucleotide as the probe, coincubation with Phox2a-specific antibody generated a supershifted band in a dose-response manner (FIG. 5C; lanes 1 to 4). When the radiolabeled PBS2 oligonucleotide was used as the probe, coincubation of SK-N-BE(2)C nuclear extracts with Phox2a-specific antibody diminished formation of CII and generated a supershifted band in a dose-dependent manner (FIG. 5C; lanes 6 to 9). In contrast, coincubation with specific antibodies against Sp1 (FIG. 5C; lane 9) or AP2 (FIG. 5C; lane 10) neither diminished CII nor generated a supershifted band. Coincubation of Phox2a-specific antibody with nuclear proteins from CATH.a or PC12 cells similarly resulted in generation of a robust supershifted band. In contrast, coincubation with preimmune serum or nuclear extracts from C6 or HeLa cells did not produce any detectable signal of supershifted band using either radiolabeled PBS1 or PBS2 oligonucleotide. Taken together, these data indicate that Phox2a is directly involved in formation of CII.

Figures 1, 5D:
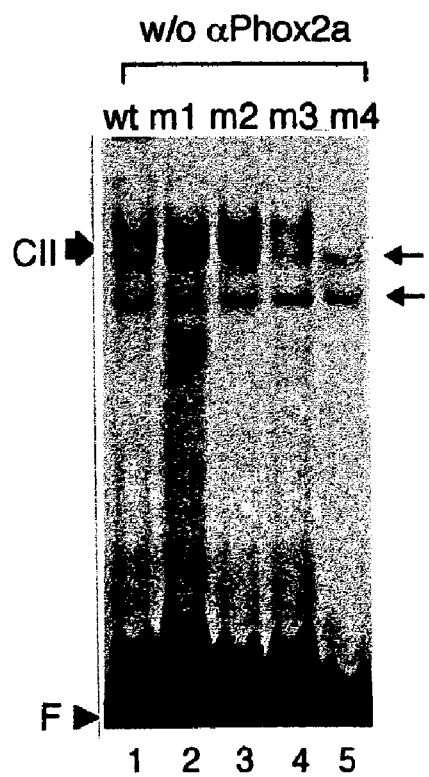
FIG. 5D is a series of photographs of autoradiographs showing the determination of nucleotide bases important for domain II (PBS2)-protein interaction in the absence (left panel) or presence (right panel) of Phox2a-specific antibody. The supershifted complex is indicated by an arrowhead. Two nonspecific bands are indicated by arrows.
Figures 2, 5D:
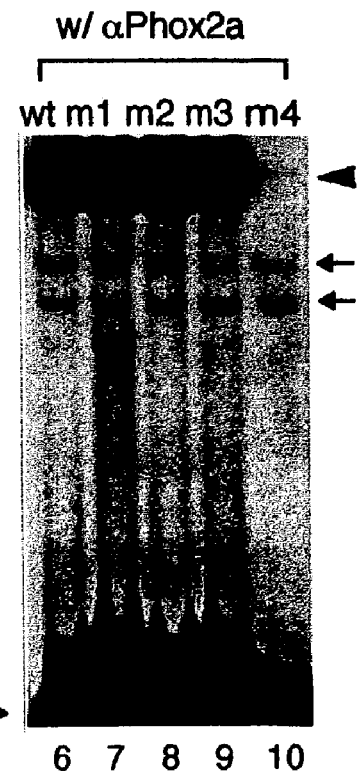

The signals of the supershifted band were significantly stronger than those of original DNA-protein complexes using either PBS1 or PBS2 probe. In the supershift assay using wild type and mutant PBS2 oligonucleotides, all probes except m4 formed a robust supershifted band, strongly suggesting that the ATTA motif is the only subregion that is essential for interaction of PBS2 with Phox2a (FIG. 5D). Similar results were obtained using lower amounts of antibodies. Although the m3 mutant did not itself form intact amounts of DNA-protein complexes, it was able to generate a supershifted band with a comparable signal (FIG. 5D; compare lanes 4 and 9 with 1 and 6). One interpretation for this finding is that m3 has comparable affinity to Phox2a but does not bind to other binding proteins as efficiently as the wild type PBS2. Alternatively, association of Phox2a with the specific antibody may have overcome its low affinity to m3 sequence.

EXAMPLE 7

Figure 6A:
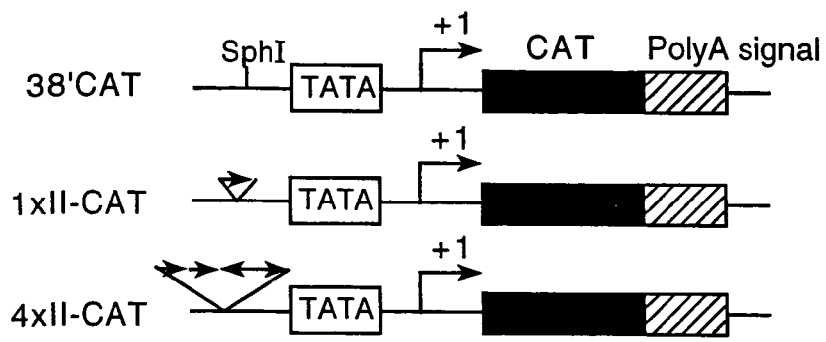
FIG. 6A is a diagram of reporter plasmids. 38'CAT is a minimal DBH-CAT reporter plasmid that contains the TATA box and the transcription start site of the human DBH gene. A single copy of domain II (PBS2) oligonucleotide is cloned at the SphI site upstream of the TATA box, resulting in 1xII-CAT. Likewise, four tandem copies of domain II (PBS2) oligonucleotide are cloned at the SphI site. Sequence analysis of 4xII-CAT showed that, among the four copies of domain II (PBS2), the third copy was in opposite orientation as indicated by the direction of arrows.
Figure 6B:
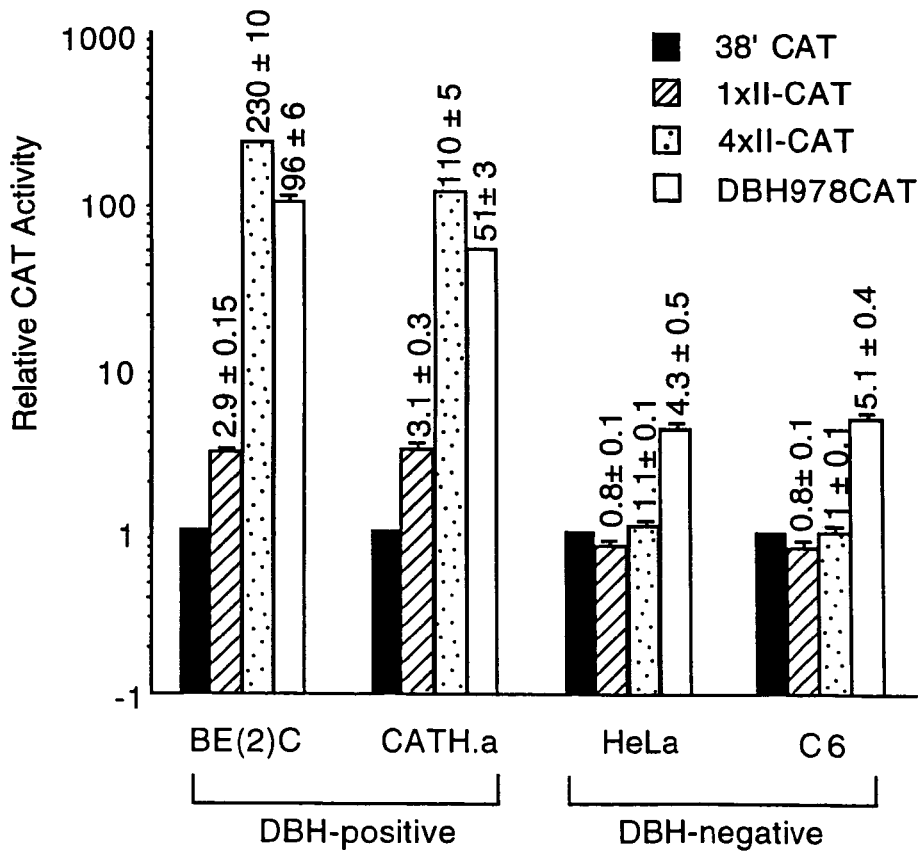
FIG. 6B is a schematic illustration showing that domain II (PBS2) sequence motifs can activate the promoter activity in a noradrenergic-specific manner. The CAT activity driven by each construct is presented relative to that of 38'CAT, with mean±SEM for six to eight determinations plotted on a logarithmic scale. This experiment was repeated once more in triplicate, using plasmid DNAs independently prepared, and resulted in similar patterns.
Figure 6C:
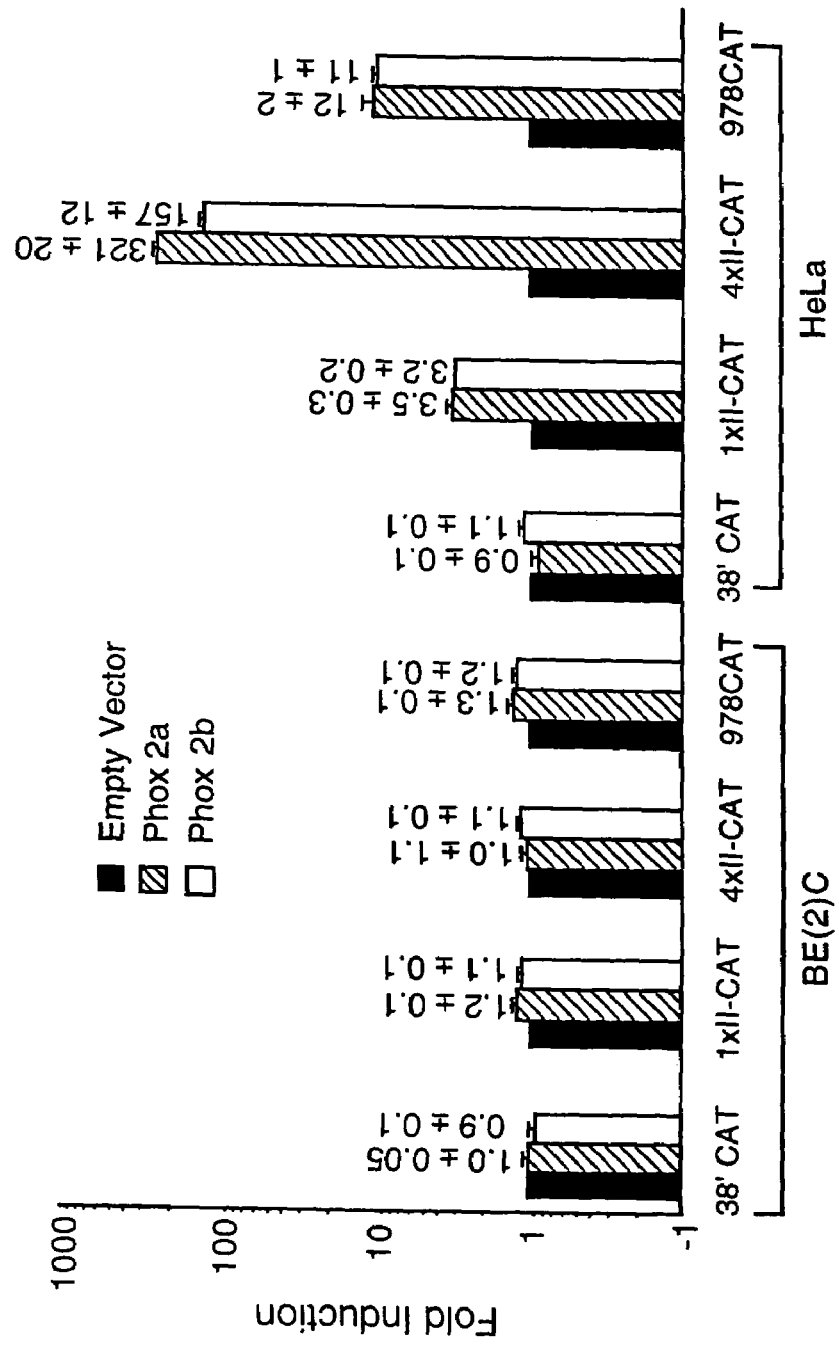
FIG. 6C is a schematic illustration showing that domain II (PBS2) can mediate transactivation by Phox2a and Phox2b. HeLa and SK-N-BE(2)C cells were transiently cotransfected with reporter plasmids and pRC/Phox2a or pRC/Phox2b with a molar ratio of 0.5. The CAT activity driven by each reporter construct itself was set to 1.0 to compare transactivation by Phox2a or Phox2b. Fold induction by Phox2a/Phox2b cotransfection is presented as mean±SEM values from six to eight samples on a logarithmic scale.

PBS2 Upregulates the DBH Minimal Promoter Activity in a Noradrenergic-Specific Manner and Mediates Phox2a/Phox2b-Induced Transcriptional Activation A single copy of PBS2 was subcloned in the correct orientation in front of the minimal promoter region of the DBH gene containing the TATA box and transcription start site (1xII-CAT; FIG. 6A), and its transcriptional activity was examined by transient transfection assays in DBH-positive and -negative cell lines. As shown in FIG. 6B, 1xII-CAT drives expression of the reporter gene 3-fold higher than that driven by 38'CAT in DBH-expressing SK-N-BE(2)C and CATA.a cells, but not in DBH-negative HeLa and C6 cells. Furthermore, cotransfection assay shows that Phox2a or Phox2b activates the reporter gene expression driven by 1xII-CAT plasmid 3- to 4-fold in DBH-negative HeLa (FIG. 6C) and C6 cells. In DBH-expressing cell lines, in contrast, cotransfection of Phox2a or Phox2b activated the promoter activity of 1xII-CAT construct only marginally, if at all (FIG. 6C). These data confirm that PBS2 is a noradrenergic-specific enhancer that mediates Phox2a-responsive transcriptional activation. The promoter activity of a single copy of PBS2 by itself, however, represented only 5% of the intact DBH promoter activity in the DBH-positive cell lines (FIG. 6B). To address whether multiple copies of PBS2 could synergistically activate the DBH minimal promoter activity in a cell-specific manner, we subcloned four tandem copies of PBS2 using the same 38'CAT plasmid (FIG. 6A). The resulting plasmid, 4xII-CAT plasmid, increased the DBH minimal promoter activity by 100- to 200-fold in DBH-positive cell lines. Thus, four tandem copies of PBS2 exhibited at least 2-fold of the promoter activity of the intact DBH promoter-enhancer region in our transient transfection assay. Strikingly, in DBH-negative cell lines the CAT activity driven by 4xII-CAT plasmid was comparable to that of 38'CAT, demonstrating a tight cell specificity. Furthermore, cotransfection with Phox2a/Phox2b-expression plasmid increased CAT activity by 200- to 300-fold only in DBH-negative cell lines. These results suggest that multiple copies of PBS2, domain IV, or a combination thereof, may be used for targeted transgene expression to noradrenergic neurons. Additionally, the multimerization of any enhancer domain that binds Phox2a or Phox2b would likely result in robust, noradrenergic cell-specific expression.

Figure 6D:
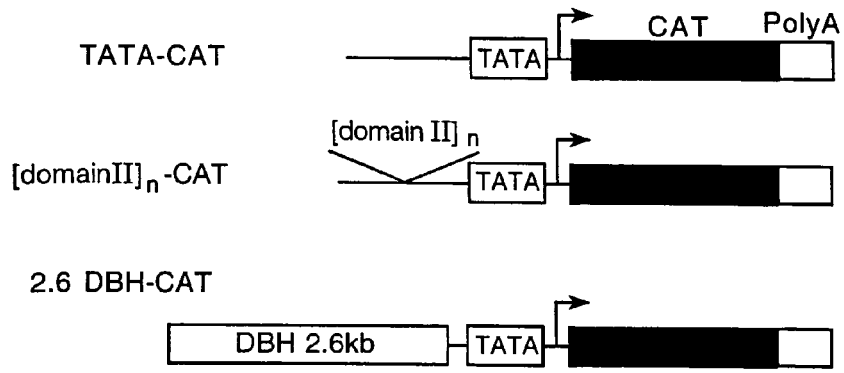
FIG. 6D is a diagram of reporter plasmids. TATA-CAT is a minimal DBH-CAT reporter plasmid that contains the TATA box and the transcription start site of the human DBH gene. DBH2.6kb-CAT contains the 2.6 kb promoter sequence of the human DBH gene. [domain II (PBS2)]n-CAT contains domain II sequence at a copy number of n, operably linked to the minimal DBH promoter.
Figure 6E:
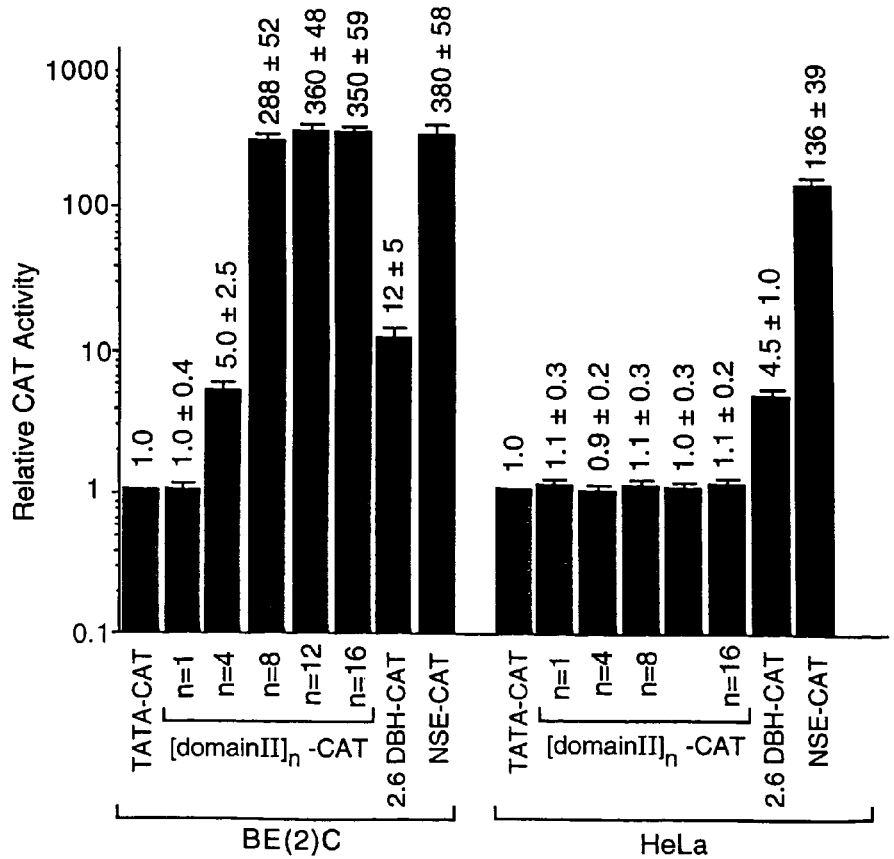
FIG. 6E shows the results of transient transfection assays of the reporter plasmids shown in FIG. 6D into DBH-positive BE(2)C cells and DBH-negative HeLa cells. The normalized CAT activity from each construct is presented relative to TATA-CAT, with mean±SEM for six to eight determinations.

In the foregoing example, the four copies of PBS2 were continuous (i.e., there was no linker sequence between each PBS2). We repeated the experiments using between 1 and 16 copies of PBS2, but this time the domains were separated by the linker sequence 5'-AGATCC-3' (SEQ ID NO: 5). As shown in Table 1, 16 copies of PBS2, operably linked to a promoter from the human DBH gene, increased promoter activity 2000-fold, and greater than 20-fold the promoter activity exhibited by DBH978CAT. A similar result was also acheived with multimerized PBS2 in which there was no spacer sequence (Figure; in this example, the maximal increase was about 350-fold with 16 copies (FIGS. 6D and 6E).

TABLE 1

| Number of copies of PBS2 | Noradrenergic cell lines | Nonneuronal cell lines |
|---|---|---|
| 1 | 1 | 1 |
| 4 | 12 | 1 |
| 8 | 1000 | 1 |

TABLE 1-continued

| Number of copies of PBS2 | Noradrenergic cell lines | Nonneuronal cell lines |
| --- | --- | --- |
| 12 | 2000 | 1 |
| 16 | 2000 | 1 |

EXAMPLE 8

Multimerized DBH Enhancers Confer Robust and Cell-specific Expression In Vivo

Figure 7A:
FIG. 7A is a diagram of recombinant adenoviral vectors. A green fluorescent protein (GFP) gene under the CMV promoter was incorporated into all backbones to allow for direct observation of the location and efficiency of infection in brain.
Figure 7A:
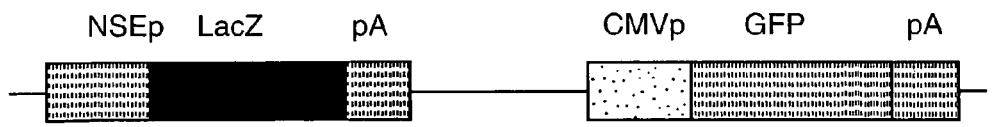
Figure 7A:
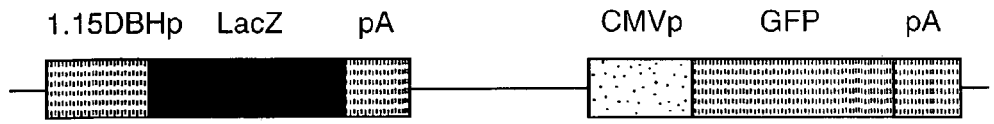

We constructed an adenoviral vector in which eight copies of PBS2 were operably linked to the minimal DBH promoter and the lacZ gene (FIG. 7A). This vector (or a control vector) was then stereotactically injected into the locus caeruleus, cerebellum, or dentate gyrus. Four days later, the expression of the lacZ reporter gene was determined by X-gal staining. The animals injected with the adenoviral vector containing the multimerized PBS2 had showed robust expression in regions in which noradrenergic cells are found, an no expression elsewhere (FIG. 7B). From these data, we conclude that infection with expression vectors containing multimerized DBH enhancer domains results in strong expression (i.e., greater than that achieved with the 2.6 kb DBH proximal sequence) in noradrenergic cells and very little or no expression elsewhere. This noradrenergic cell-specific was not observed with the vector containing the 2.6 kb DBH proximal sequence (FIG. 7B).

EXAMPLE 9

Identification of a Phox2a binding Site

DNAse I footprinting analysis using a purified $His_6$-Phox2a (1–149) fusion protein revealed an additional Phox2A binding site at –105 to –85 of the DBH proximal region (5'-GAGGGAAAATTGGATTCCCCG-3' (SEQ ID NO: 6); PBS3). (The term "PBS3" is equivalent to the old terminology "PBD3".) We performed a mutagenesis analysis of this site. Two mutant constructs were made. We predicted that the first (5'-GAGGGAAAGCCTTCGGC CCCG-3' (SEQ ID NO: 7); mPBS3) would abolish Phox2A binding, and the second (5'-GAGGGAAAATTGGATTAC-CCG-3' (SEQ ID NO: 8); mPBS3(ATTA)) would improve binding. Each of these predictions was realized (Table 2).

TABLE 2

|  | BE | M17 | HeLa | C6 | HepG2 |
| --- | --- | --- | --- | --- | --- |
| Wt | 2.4 | 3.2 | 0.1 | 0.2 | 0.04 |
| mPBS3 | 0.12 | 0.32 | 0.08 | 0.14 | 0.027 |
| mPBS3 (ATTA) | 28.8 | 21.1 | 0.11 | nd | 0.04 |

EXAMPLE 10

Optimization of Phox2a Binding Sites

Based on our findings, it is likely that the endogenous Phox2a binding sites are not optimized. Optimization can be performed using the methods described herein. In one example, PBS2 is systematically altered and tested for expression levels and cell specificity. Optimized enhancer domains are useful as multimerized enhancer domains, as is described throughout the specification. They are also useful in the intact promoter. For example, it may be desirable to use the 1.1 kb or 2.6 kb proximal region for the production of a transgenic animal (e.g., a transgenic mouse) for the purposes of, for example, drug screening. In this context, one or more Phox2a binding sites can be altered to optimize or improve Phox2a binding or Phox2a-mediated transcription. Preferably, the binding or transcription is improved at least two-fold.

EXAMPLE 11

Figure 8:
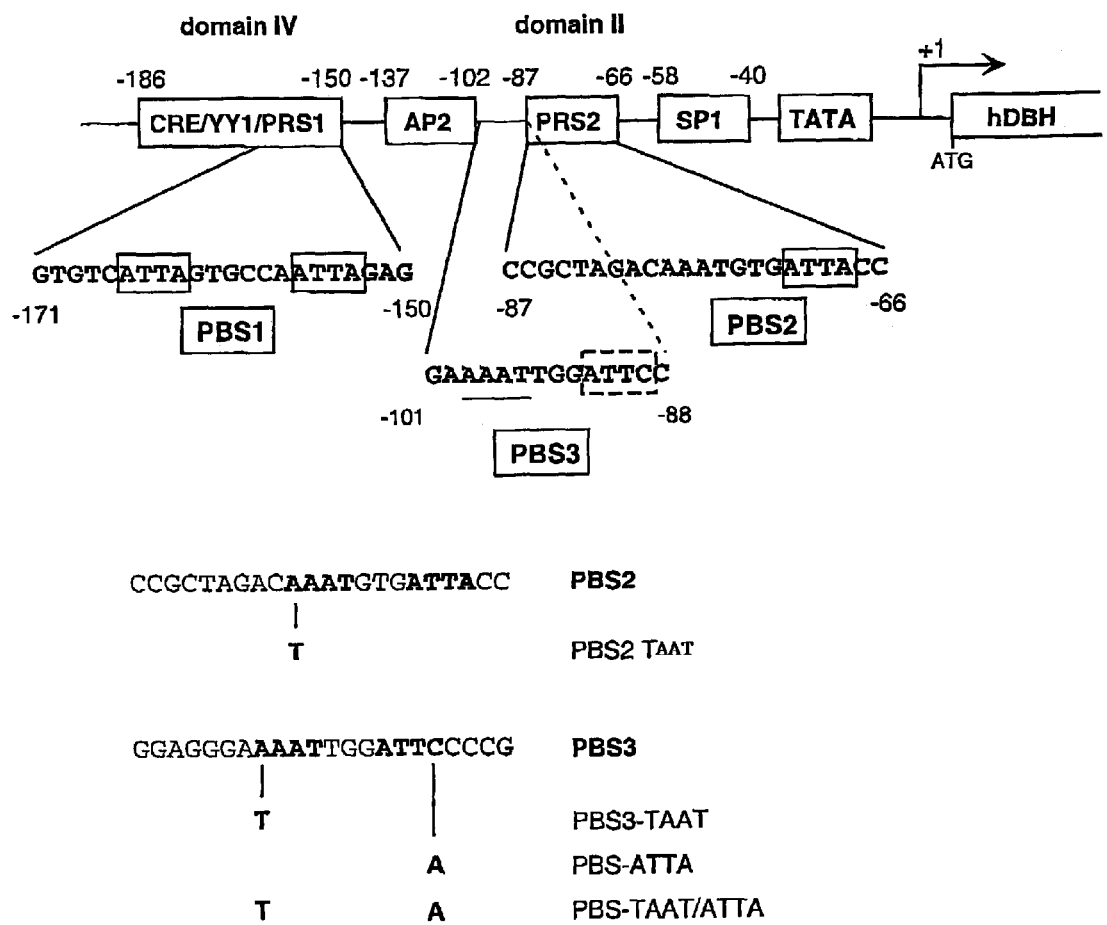
FIG. 8 shows the Phox2a binding sites in the 5' proximal area of human DBH gene, and the wild-type and consensus sequences of PBS2 (domain II) and PBS3.
Figure 9:
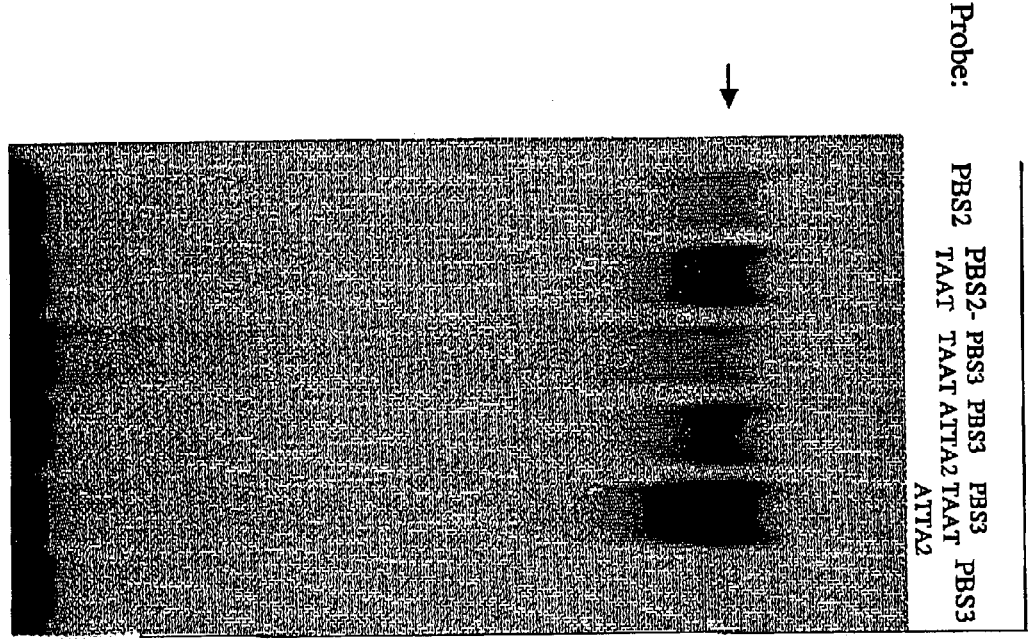
FIG. 9 is a photograph of a gel mobility shift assay for both wt and the mutants for homeodomain motifs in PBS2 and 3. Five microliters of in vitro translated Phox2a out of 50 μL reaction was used for the binding reaction with 40,000 cpm of each labeled oligonucleotide. The nucleotide sequences of the oligonucleotide used in the experiment was shown in FIG. 9.
Figure 10:
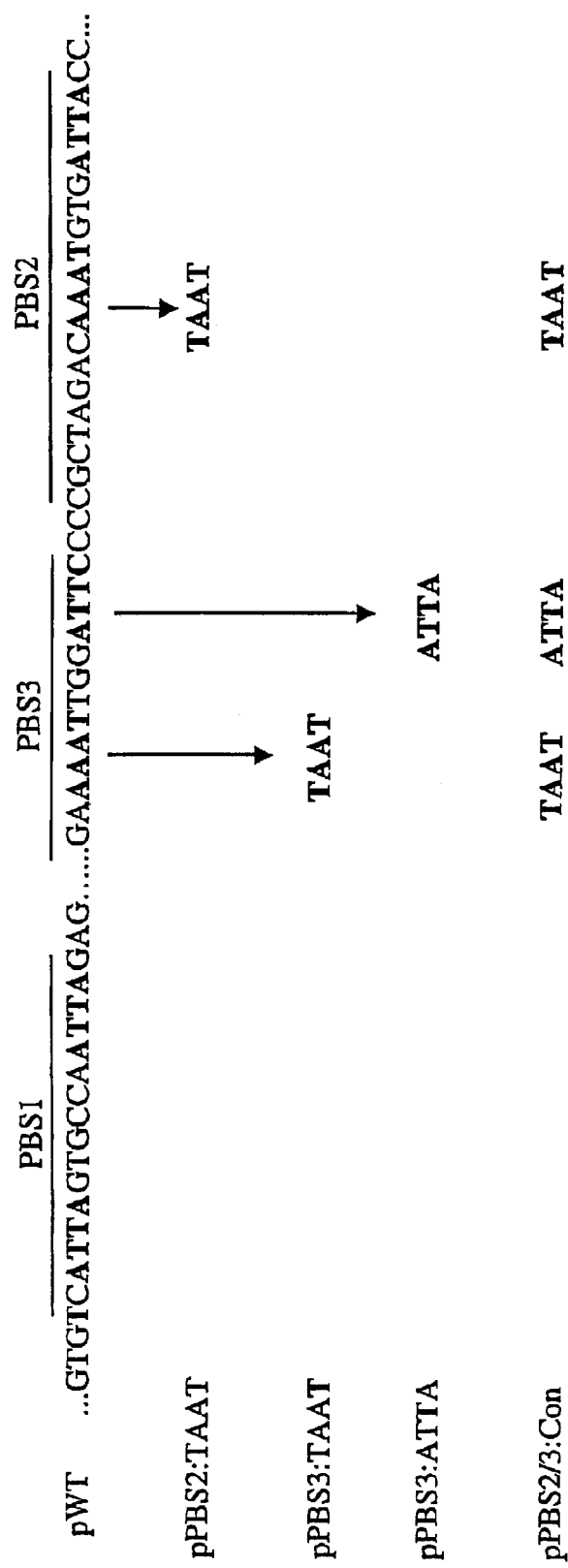
FIG. 10 shows the sequences of PBS1, 2 and 3 of wild-type and mutant hDBH promoters used in our transient expression studies described in FIG. 11.
Figure 11:
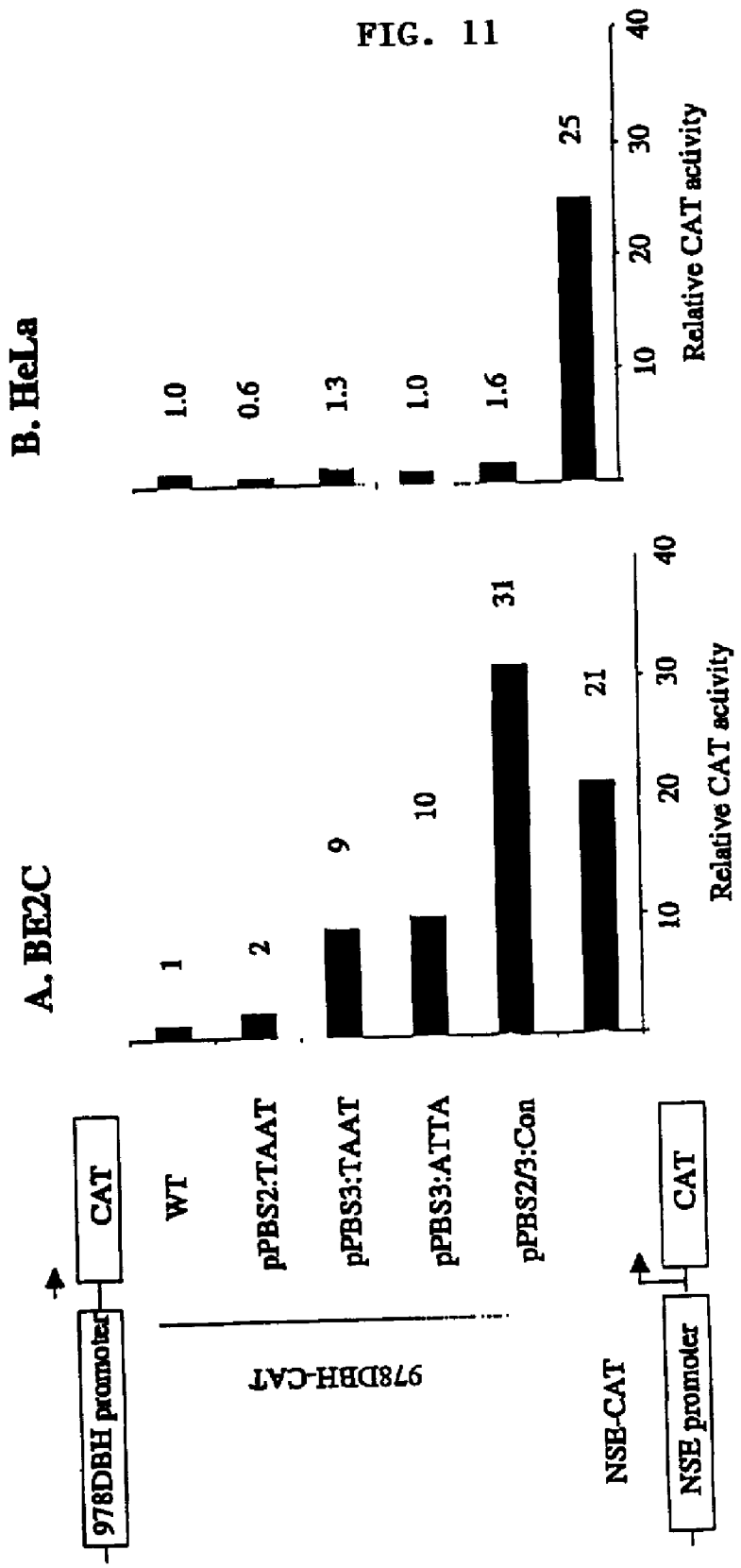
FIG. 11 depicts the transcription activities of the hDBH promoter transiently expressed in both Phox2a-positive (BE2C) and negative (Hela) cells. Transcription activities of CAT reporter plasmids were compared in SK-N-BE(2)C (A) and Hela (B) cell lines. X-axis denotes 'fold basal CAT activity' which was determined by dividing the normalized CAT activity from each construct by that from the wt 978DBH promoter-CAT. The CAT activity from the wt DBH promoter is set to 1.0

Conversion of Imperfect Homeodomain Motifs in PBS2 and PBS3 to the Palindromic Consensus Sequence Enhances Both the Binding of Phox2a and the Expression of DBH While PBS1 contains consensus homeodomain motifs (ATTA), PBS2 and PBS3 have imperfect motifs (FIG. 8). One and both core motifs in the palindromic structure of PBS2 and PBS3, respectively, have a nucleotide deviated from the consensus sequence ("ATTA" or "TAAT") (FIG. 8). To generate a better binding site for Phox2a, we changed the deviated nucleotides of PBS2 and PBS3 individually or in combination toward consensus sequences (FIG. 8). When examined by gel shift assay, the mutated PBSs (PBS2-TAAT, PBS3-TAAT, PBS3-ATTA, and PBS3-TAAT/ATTA) showed increased binding to Phox2a than to native PBS2 or PBS3 (FIG. 9). The mutated PBSs have the following sequence. PBS2-TAAT: 5'-CCGCTAGACTAATGTGAT-TACC-3' (SEQ ID NO: 39); PBS3 -TAAT: 5'-GAGG-GATAATTGGATTCCCCG-3' (SEQ ID NO: 40); PBS3-ATTA: 5'-GAGGGAAAATTGGATTACCCG-3' (SEQ ID NO: 8); and PBS3-TAAT/ATTA: 5'-GAGGGATAATTG-GATTACCCG-3' (SEQ ID NO: 41). Among them, PBS3-TAAT/ATTA retained highest affinity to Phox2a. To examine if these modified binding sites augment transcriptional activities of hDBH promoter, we converted imperfect homeodomain motifs of PBS2 and PBS3 into consensus motifs individually or together in hDBH promoter context (FIG. 10). When tested in Phox2a-positive cell line BE2C, modification of PBS2 and PBS3 sequences enhanced promoter activity of hDBH promoter. Particularly, the promoter with consensus motifs in all three PBSs showed about 31-fold higher activity than wt 978hDBH promoter (FIG. 11). These newly introduced consensus motifs did not affect the promoter activity significantly in Phox2a negative cell lines (FIG. 11).

The foregoing results were obtained with the following methods.

Cell Culture and Transient Transfection Assays

Human neuroblastoma SK-N-BE(2)C and SK-N-BE(2) M17 and mouse central noradrenergic neuron-derived CATH.a cell lines were maintained as described (Kim et al., J. Neurosci., 14:7200–7207, 1994; Ishiguro, supra; Suri et al., J. Neurosci. 13:1280–1291, 1993) and used as the DBH-positive system. The HeLa and rat C6 glioma cell lines were grown in Dulbecco's modified Eagle's medium supplemented with 10% fetal calf serum, streptomycin, and penicillin and used as the DBH-negative system in this study.

Transfection was performed by the calcium phosphate coprecipitation method as previously described (Ishiguro, supra; Seo et al., J. Neurosci., 16:4102–4112, 1996). For the SK-N-BE(2)C and SK-N-BE(2)M17 cell lines, each 60-mm dish was transfected with 2 mg of the reporter construct, 1 mg of pRSV-β gal, varying amounts of the effector plasmid, and pUC19 plasmid to a total of 5 mg DNA. For the other cell lines, twice as much DNA was used in transfection. Plasmids used for transient transfection assays were prepared using Qiagen columns (QIAGEN Inc., Santa Clarita, Calif.). To correct for differences in transfection efficiencies among different DNA precipitates, CAT activity was normalized to that of β-galactosidase. CAT and β-galactosidase activities were assayed as previously described (Ishiguro, supra; Seo, supra).

DNA Constructions

The DBH978CAT and DBH262CAT reporter constructs contain the 978 bp and 262 bp upstream sequences of the human DBH gene, respectively, fused to the bacterial CAT gene (Ishiguro, supra). A series of human DBH promoter-CAT reporter constructs with progressive deletions of proximal protein-binding sites were generated using pBLCAT3-1, which drives significantly lower background CAT activity compared to pBLCAT3 (Luckow and Schutz, Nucl. Acids. Res., 15:5490, 1987). 262'CAT construct was generated by ligating the 271 bp SphI-XbaI fragment of 262CAT plasmid with the 4.3 kb SphI-XbaI backbone of pBLCAT3-1 plasmid. 114'CAT construct was made by ligating the 726 bp HindIII-NcoI fragment with HindIII-NcoI backbone of pBLCAT3-1 plasmid. To generate 142'CAT and 62'CAT plasmids, polymerase chain reaction was performed using oligonucleotides 5'-GACATGCATGCGCAGGCTGAGT-GCTTGGC-3' (SEQ ID NO: 9) and 5'-CATTTTAGCTTC-CTTAGC-3' (SEQ ID NO: 10), and 5'-GACATGCAT-GCGCTGCCTGGACCCACCCC-3' (SEQ ID NO: 11) and 5'-CATTTTAGCTTCCTTAGC-3' (SEQ ID NO: 12), respectively, using DBH978CAT as the template. The 163 bp and 71 bp fragments were isolated after digesting the PCR products with SphI and XbaI, and then subcloned into pBLCAT3-1 that had been digested with SphI and XbaI, resulting in 142'CAT and 62'CAT plasmids, respectively. 38'CAT plasmid was constructed as follows: polymerase chain reaction was performed using oligonucleotides 5'-GA-CATGCATGCGTCCAGGGCATAAATGGC-3' (SEQ ID NO: 13) and 5'-CATTTTAGCTTCCTTAGC (SEQ ID NO: 14) and DBH978CAT plasmid as the template. A 70 bp fragment was isolated after digesting the PCR product with SphI and XhoI and subcloned to pBLCAT3-1 that had been digested with SphI and XhoI. pBLCAT3-1 is a derivative of pBLCAT3 and was constructed by deleting the CRE-like sequence and TATA-like sequence upstream of multiple cloning sites. The resultant plasmid 38'CAT, containing the TATA box and transcription start site of the human DBH gene fused to the CAT gene, was isolated and confirmed by sequence analysis. Upstream sequences and junction regions of these deletional constructs were confirmed by sequencing analysis.

Base substitutions were generated in the context of the 978 bp upstream sequence using the QuickChangeTM PCR-based site-directed mutagenesis kit (Stratagene, La Holla, Calif.) according to the manufacturer's procedure. The following oligonucleotides were used in the mutagenesis procedure using DBH978CAT plasmid as the template: 5'-CCTGGACCCACTATGTTCAGGACCAG-3' (SEQ ID NO: 15) and 5'-CCTGGTCCTGAACATAGTGGGTCCAG-3' (SEQ ID NO: 16) for domain I mutant, 5'-CCGCTAGA-CAAGCAGACGTACCCGTGCTG-3' (SEQ ID NO: 17) and 5'-GCAGCACGGGTACGTCTGCTTGTCTAGCG- 3' (SEQ ID NO: 18) for PBS2 mutant, and 5'-TGAGTGCT-TGGCCTGGTTAGCAAGCTTGTGGGAGG-3' (SEQ ID NO: 19) and 5'-CCCTCCCACAAGCTTGCTAACCAG-GCCAAGCACTC-3' (SEQ ID NO: 20) for domain III mutant. For domain IV, the following primers were used: 5'-CCATGTGTCACCGGTGCCAATTAG-3' (SEQ ID NO: 21) and 5'-CTAATTG GCACCGGTGACACATGG-3' (SEQ ID NO: 22) for mHD1, 5'-CATTAGTGCC AACCGGAG-GAGGGC-3' (SEQ ID NO: 23) and 5'-GCCCTCCTCCG-GTTGG CACTAATG-3' (SEQ ID NO: 24) for mHD2. 5'-CACCGGTGCCAACCGGAG GAGGGCAG'3' (SEQ ID NO: 25) and 5'-GCTGCCCTCCTCCGGTTGGCAC CGGT-3' (SEQ ID NO: 26) were used to produce mHD1+2 using mHD1 as the template. In each case, the first set of primers represents coding strand sequences containing the desired mutations, and the second set of primers represents the corresponding noncoding strand sequences. Constructs with correct mutations were screened by restriction enzyme digestion and sequencing analysis.

A single copy of the PBS2 oligonucleotide (see below) was subcloned to the SphI site of 38'CAT plasmid. After restriction and sequencing analyses, the 1xII-CAT construct containing a single copy of PBS2 in correct orientation was selected. In addition, the same PBS2 oligonucleotide was ligated after Klenow reaction. A DNA fragment of 92 bp was isolated and subcloned to the same SphI site of 38'CAT plasmid. 4xII-CAT plasmid, which contains four copies of PBS2 (three copies in the right orientation and one in the opposite orientation; FIG. 6), was isolated and confirmed by sequence analysis. Recombinant constructs that can express Phox2a or Phox2b were used as effector plasmids. pRc/Phox2a containing the full length cDNA for Phox2a under the control of the CMV promoter has been described previously (Valarche, supra). A full-length cDNA fragment encoding Phox2b was isolated by digesting pBluescript KS II+/Phox2b (Pattyn et al., Development, 125: 599–608, 1997) with HindIII and ApaI, and was subcloned downstream of the CMV promoter using the same pRC/CMV vector, resulting in pRC/Phox2b.

In Vitro Transcription and Translation

The TNT coupled Wheat Germ Extract Transcription/Translation System (Promega, Madison, Wis., USA) was used to generate in vitro translated Phox2a proteins according to the manufacturer's protocol. For the wild-type and mutant (sou$^{m811}$ and sou$^{m812}$) zPhox2a, pczPhox2a constructs were digested with SalI restriction enzyme, which has restriction site at 30 amino acid after HD, to make zPhox2a (1–181) protein. For murine Phox2a proteins, pcPhox2a (1–222) and pcPhox2a (90–149) were digested with XhoI restriction enzyme, and were in vitro transcribed and translated. The proteins were expressed with or without [$^{35}$S]methionine. For cotranslation experiments, the amount of each template was reduced by one-half for the same volume reaction. Expressed proteins were analyzed by 15% SDS-PAGE, followed by autoradiography, EMSA, and antibody coincubation experiments.

Expression and Purification of Hexahistidine His$_6$-Phox2a (1–149)

The recombinant His$_6$-Phox2a (1–149) fusion protein was constructed by inserting the N-terminal portion (amino acids 1–149) of murine Phox2a cDNA into the pET15b expression vector (Novagen, Madison, Wis., USA). The following oligonucleotides were used as primers for the amplification of the coding region by PCR: 5'-GGATCCATATGGAC-TACTCCTACCTCAATTC-3' (SEQ ID NO: 37) and 5'-AAAAACTCGAGTTATTTGGCCGTGGC-CGCGCGCTC-3' (SEQ ID NO: 38) using pRc/Phox2a as a template. The His$_6$-Phox2a (1–149) expressed in BL21 (DE3) cells was eluted by stepwise decrease in pH (pH 8.0-pH 4.5 in 8 M urea, 0.1 M sodium phosphate, 0.01 M Tris/HCI) on $Ni^{2+}$-chelated affinity resin. To maximize renaturation, purified $His_6$-Phox2a (1–149) was dialyzed by stepwise decrease in concentration of urea to zero in the final buffer (12 mM HEPES, 5% glycerol, 5 mM $MgCl_2$, 60 mM KCl, 1 mM EDTA, 100 µg/mL bovine serum albumin (BSA), 0.1% Nonidet NP-40). $His_6$-Phox2a (1–149) fusion protein was purified to an apparent homogeneity at pH 4.8.

Preparation of Nuclear Extracts, EMSA, and DNase I Footprinting

Nuclear extracts were prepared from different cell lines according to the procedure described by (Dignam et al., Nucl. Acid Res., 11:1475–1489, 1983). Sense and antisense oligonucleotides corresponding to the sequences of domains I, II, and III were synthesized, and the sense and antisense oligonucleotides were annealed, gel-purified Nuclear, and $^{32}P$-labeled by T4 DNA kinase and used as probes in electrophoretic mobility shift assays (EMSA). EMSA and antibody coincubation experiments were performed using 30,000 to 50,000 cpm of labeled probe (approximately 0.05 to 0.1 ng) and nuclear extracts (10 to 30 mg) in a final volume of 20 mL of 12.5% glycerol, 12.5 mM HEPES (pH 7.9), 4 mM Tris-HCl (pH 7.9), 60 mM KCl, 1 mM EDTA, and 1 mM DTT with 1 mg of poly(dI-dC). Competition binding assays were performed by adding nonradioactive competitor oligonucleotides in a molar excess prior to adding $^{32}P$-labeled oligonucleotides. For supershift assay, antibody was coincubated with the nuclear extract mix for 30 min at room temperature prior to adding the radiolabeled probe. Antibodies against Sp1, Sp3, Sp4, and AP2 were purchased from Santa Cruz Biotechnology, Inc. (Santa Cruz, Calif.). A Phox2a-specific antibody (#60) raised against a polypeptide (Y75 to R88) residing immediately upstream of the HD was used in the supershift assay. Recombinant AP2 proteins were purchased from Promega Corporation (Madison, Wis.) and used for EMSA with $^{32}P$-labeled DIII oligonucleotide and consensus AP2 sequence as probes. DNase I footprinting assay was performed using the wild type and mutant human DBH 5' proximal fragments that had been prepared by polymerase chain reaction as the probe as described (Seo, supra). After incubating approximately 30,000 cpm of labeled probe with 150–200 mg of nuclear extracts from different cell lines, freshly diluted DNase I (1.5 to 2.5 units) was added to a final volume of 40 mL and incubated for 90 seconds at the room temperature. The precise amount of DNase I was empirically determined for each extract to ensure an even pattern of digested bands. For the sample without nuclear extracts, much lower amounts of DNase I (approximately one tenth) were used. The probe DNA treated with DNase I was purified and an aliquot (approximately 10 to 20%) of each sample was analyzed on a 6% polyacrylamide/8M urea-sequencing gel followed by autoradiography with an intensifying screen. Location of the protected area was determined by Maxam-Gilbert sequencing of labeled probes.

Southwestern Blot Analysis

Southwestern blotting was performed as described (Michael et al., Science 239: 1531–1533, 1988). Two sets of nuclear proteins prepared from different cell lines (100 mg each per lane) were mixed with 10 mL of 2× sample loading buffer (4% SDS, 14% glycerol, 0.16 M Tris, pH 6.8, 0.1% BPB, 5 mM DTT) and buffer D (Dignam, supra) to a final volume of 20 mL, heated to 95° C. for 5 min and then separated on a denaturing SDS-10% polyacrylamide gel. The protein bands were transferred to a nitrocellulose membrane, and the nonspecific protein bands on the membrane were blocked by three washes of 45 min in 10 mM Tris, pH 7.5, 5% nonfat dry skim milk, 10% glycerol, 2.5% Nonindet P40, 0.1 mM DTT, and 150 mM NaCl at 25° C. The membrane was then rinsed briefly in binding buffer (10 mM Tris, pH 7.5, 40 mM NaCl, 1 mM EDTA, 1 mM DTT, 8% glycerol, 0.125% nonfat dry skim milk) and was incubated in 10 mL of binding buffer containing 500,000 cpm/mL end-labeled PBS2 oligonucleotide probe and 10 mg/mL poly(dI-dC). After incubation overnight at room temperature, the membranes were removed from the bag, washed with 10 mL of 10 mM Tris, pH 7.5, and 50 mM NaCl three times. The specific protein-PBS2 interactions were visualized by autoradiography. The specificity of these interactions was determined by adding a 100-fold molar excess of unlabeled PBS2 oligonucleotide to the second set of separate hybridization bag.

What is claimed is:

1. An enhancer cassette having the formula $[X-Y]_n$, wherein each X is, independently, SEQ ID NO: 40 or SEQ ID NO: 41; each Y is, independently, absent or a mono- or polynucleotide that contains between one and thirty nucleotides; and n is an integer between two and fifty, inclusive.

2. The enhancer cassette of claim 1, wherein each X is SEQ ID NO: 41.

3. The enhancer cassette of claim 1, wherein Y is absent or is a mono- or polynucleotide that contains between one and six nucleotides, inclusive.

4. The enhancer cassette of claim 1, further comprising an RNA polymerase binding site and a transcription initiation site.

5. The cassette of claim 1, wherein n is greater than four.

6. The cassette of claim 5, wherein n is greater than eight.

7. The cassette of claim 6, wherein n is greater than nine.

8. An expression vector comprising an enhancer cassette having the formula $[X-Y]_n$, wherein each X is independently SEQ ID NO: 40 or SEQ ID NO: 41; each Y is, independently, absent or a mono or polynucleotide that has between one and thirty nucleotides; and n is an integer between one and fifty, inclusive.

9. A method of expressing a nucleic acid molecule in a noradrenergic cell, comprising expressing in said noradrenergic cell an expression vector comprising an enhancer cassette having the formula $[X-Y]_n$ operably linked to said nucleic acid molecule, wherein each X is independently SEQ ID NO: 40 or SEQ ID NO: 41; each Y is, independently, absent or a mono- or polynucleotide that has between one and thirty nucleotides; and n is an integer between three and fifty, inclusive.

* * * * *

SEQUENCE LISTING

<160> NUMBER OF SEQ ID NOS: 41

<210> SEQ ID NO 1
<211> LENGTH: 22
<212> TYPE: DNA
<213> ORGANISM: Homo sapiens

<400> SEQUENCE: 1
gtgtcattag tgccaattag ag          22

<210> SEQ ID NO 2
<211> LENGTH: 22
<212> TYPE: DNA
<213> ORGANISM: Homo sapiens

<400> SEQUENCE: 2
ccgctagaca aatgtgatta cc          22

<210> SEQ ID NO 3

-continued

```
<211> LENGTH: 8
<212> TYPE: DNA
<213> ORGANISM: Homo sapiens

<400> SEQUENCE: 3 tgacgtcc                                                                 8

<210> SEQ ID NO 4
<211> LENGTH: 8
<212> TYPE: DNA
<213> ORGANISM: Homo sapiens

<400> SEQUENCE: 4 tgacgtca                                                                 8

<210> SEQ ID NO 5
<211> LENGTH: 6
<212> TYPE: DNA
<213> ORGANISM: Homo sapiens

<400> SEQUENCE: 5 agatcc                                                                   6

<210> SEQ ID NO 6
<211> LENGTH: 21
<212> TYPE: DNA
<213> ORGANISM: Homo sapiens

<400> SEQUENCE: 6
gagggaaaat tggattcccc g                                                 21

<210> SEQ ID NO 7
<211> LENGTH: 21
<212> TYPE: DNA
<213> ORGANISM: Artificial Sequence
<220> FEATURE:
<223> OTHER INFORMATION: Based on Homo sapiens

<400> SEQUENCE: 7
gagggaaagc cttcggcccc g                                                 21

<210> SEQ ID NO 8
<211> LENGTH: 21
<212> TYPE: DNA
<213> ORGANISM: Artificial Sequence
<220> FEATURE:
<223> OTHER INFORMATION: Based on Homo sapiens

<400> SEQUENCE: 8
gagggaaaat tggattaccc g                                                 21

<210> SEQ ID NO 9
<211> LENGTH: 29
<212> TYPE: DNA
<213> ORGANISM: Homo sapiens

<400> SEQUENCE: 9
gacatgcatg cgcaggctga gtgcttggc                                         29

<210> SEQ ID NO 10
<211> LENGTH: 18
<212> TYPE: DNA
<213> ORGANISM: Homo sapiens

<400> SEQUENCE: 10
```

-continued

```
cattttagct tccttagc                                              18

<210> SEQ ID NO 11
<211> LENGTH: 29
<212> TYPE: DNA
<213> ORGANISM: Homo sapiens

<400> SEQUENCE: 11
gacatgcatg cgctgcctgg acccacccc                                  29

<210> SEQ ID NO 12
<211> LENGTH: 18
<212> TYPE: DNA
<213> ORGANISM: Homo sapiens

<400> SEQUENCE: 12
cattttagct tccttagc                                              18

<210> SEQ ID NO 13
<211> LENGTH: 29
<212> TYPE: DNA
<213> ORGANISM: Homo sapiens

<400> SEQUENCE: 13
gacatgcatg cgtccagggc ataaatggc                                  29

<210> SEQ ID NO 14
<211> LENGTH: 18
<212> TYPE: DNA
<213> ORGANISM: Homo sapiens

<400> SEQUENCE: 14
cattttagct tccttagc                                              18

<210> SEQ ID NO 15
<211> LENGTH: 26
<212> TYPE: DNA
<213> ORGANISM: Artificial Sequence
<220> FEATURE:
<223> OTHER INFORMATION: Based on Homo sapiens

<400> SEQUENCE: 15
cctggaccca ctatgttcag gaccag                                     26

<210> SEQ ID NO 16
<211> LENGTH: 26
<212> TYPE: DNA
<213> ORGANISM: Artificial Sequence
<220> FEATURE:
<223> OTHER INFORMATION: Based on Homo sapiens

<400> SEQUENCE: 16
cctggtcctg aacatagtgg gtccag                                     26

<210> SEQ ID NO 17
<211> LENGTH: 29
<212> TYPE: DNA
<213> ORGANISM: Artificial Sequence
<220> FEATURE:
<223> OTHER INFORMATION: Based on Homo sapiens

<400> SEQUENCE: 17
ccgctagaca agcagacgta cccgtgctg                                  29
```

<210> SEQ ID NO 18
<211> LENGTH: 29
<212> TYPE: DNA
<213> ORGANISM: Artificial Sequence
<220> FEATURE:
<223> OTHER INFORMATION: Based on Homo sapiens

<400> SEQUENCE: 18
gcagcacggg tacgtctgct tgtctagcg                                         29

<210> SEQ ID NO 19
<211> LENGTH: 35
<212> TYPE: DNA
<213> ORGANISM: Artificial Sequence
<220> FEATURE:
<223> OTHER INFORMATION: Based on Homo sapiens

<400> SEQUENCE: 19
tgagtgcttg gcctggttag caagcttgtg ggagg                                  35

<210> SEQ ID NO 20
<211> LENGTH: 35
<212> TYPE: DNA
<213> ORGANISM: Artificial Sequence
<220> FEATURE:
<223> OTHER INFORMATION: Based on Homo sapiens

<400> SEQUENCE: 20
ccctcccaca agcttgctaa ccaggccaag cactc                                  35

<210> SEQ ID NO 21
<211> LENGTH: 24
<212> TYPE: DNA
<213> ORGANISM: Artificial Sequence
<220> FEATURE:
<223> OTHER INFORMATION: Based on Homo sapiens

<400> SEQUENCE: 21
ccatgtgtca ccggtgccaa ttag                                              24

<210> SEQ ID NO 22
<211> LENGTH: 24
<212> TYPE: DNA
<213> ORGANISM: Artificial Sequence
<220> FEATURE:
<223> OTHER INFORMATION: Based on Homo sapiens

<400> SEQUENCE: 22
ctaattggca ccggtgacac atgg                                              24

<210> SEQ ID NO 23
<211> LENGTH: 24
<212> TYPE: DNA
<213> ORGANISM: Artificial Sequence
<220> FEATURE:
<223> OTHER INFORMATION: Based on Homo sapiens

<400> SEQUENCE: 23
cattagtgcc aaccggagga gggc                                              24

<210> SEQ ID NO 24
<211> LENGTH: 24
<212> TYPE: DNA
<213> ORGANISM: Artificial Sequence
<220> FEATURE:
<223> OTHER INFORMATION: Based on Homo sapiens

```
<400> SEQUENCE: 24
gccctcctcc ggttggcact aatg                                    24

<210> SEQ ID NO 25
<211> LENGTH: 26
<212> TYPE: DNA
<213> ORGANISM: Artificial Sequence
<220> FEATURE:
<223> OTHER INFORMATION: Based on Homo sapiens

<400> SEQUENCE: 25
caccggtgcc aaccggagga gggcag                                  26

<210> SEQ ID NO 26
<211> LENGTH: 26
<212> TYPE: DNA
<213> ORGANISM: Artificial Sequence
<220> FEATURE:
<223> OTHER INFORMATION: Based on Homo sapiens

<400> SEQUENCE: 26
gctgccctcc tccggttggc accggt                                  26

<210> SEQ ID NO 27
<211> LENGTH: 20
<212> TYPE: DNA
<213> ORGANISM: Homo sapiens

<400> SEQUENCE: 27
gcctggaccc accccattca                                         20

<210> SEQ ID NO 28
<211> LENGTH: 20
<212> TYPE: DNA
<213> ORGANISM: Artificial Sequence
<220> FEATURE:
<223> OTHER INFORMATION: Based on Homo sapiens

<400> SEQUENCE: 28
gcctggaccc actatgttca                                         20

<210> SEQ ID NO 29
<211> LENGTH: 22
<212> TYPE: DNA
<213> ORGANISM: Homo sapiens

<400> SEQUENCE: 29
ccgctagaca aatgtgatta cc                                      22

<210> SEQ ID NO 30
<211> LENGTH: 22
<212> TYPE: DNA
<213> ORGANISM: Artificial Sequence
<220> FEATURE:
<223> OTHER INFORMATION: Based on Homo sapiens

<400> SEQUENCE: 30
ccgctagaca agcagacgta cc                                      22

<210> SEQ ID NO 31
<211> LENGTH: 35
<212> TYPE: DNA
<213> ORGANISM: Homo sapiens
```

<400> SEQUENCE: 31
tgagtgcttg gcctggggcg caagcttgtg ggagg					35

<210> SEQ ID NO 32
<211> LENGTH: 35
<212> TYPE: DNA
<213> ORGANISM: Artificial Sequence
<220> FEATURE:
<223> OTHER INFORMATION: Based on Homo sapiens

<400> SEQUENCE: 32
tgagtgcttg gcctggttag caagcttgtg ggagg					35

<210> SEQ ID NO 33
<211> LENGTH: 22
<212> TYPE: DNA
<213> ORGANISM: Artificial Sequence
<220> FEATURE:
<223> OTHER INFORMATION: Based on Homo sapiens

<400> SEQUENCE: 33
cctatagaca aatgtgatta cc					22

<210> SEQ ID NO 34
<211> LENGTH: 22
<212> TYPE: DNA
<213> ORGANISM: Artificial Sequence
<220> FEATURE:
<223> OTHER INFORMATION: Based on Homo sapiens

<400> SEQUENCE: 34
ccgctagcta aatgtgatta cc					22

<210> SEQ ID NO 35
<211> LENGTH: 22
<212> TYPE: DNA
<213> ORGANISM: Artificial Sequence
<220> FEATURE:
<223> OTHER INFORMATION: Based on Homo sapiens

<400> SEQUENCE: 35
ccgctagaca aacttgatta cc					22

<210> SEQ ID NO 36
<211> LENGTH: 22
<212> TYPE: DNA
<213> ORGANISM: Artificial Sequence
<220> FEATURE:
<223> OTHER INFORMATION: Based on Homo sapiens

<400> SEQUENCE: 36
ccgctagaca aatgtgatgc cc					22

<210> SEQ ID NO 37
<211> LENGTH: 31
<212> TYPE: DNA
<213> ORGANISM: Mus musculus

<400> SEQUENCE: 37
ggatccatat ggactactcc tacctcaatt c					31

<210> SEQ ID NO 38
<211> LENGTH: 35
<212> TYPE: DNA
<213> ORGANISM: Mus musculus

```
<400> SEQUENCE: 38
aaaaactcga gttatttggc cgtggccgcg cgctc                                   35

<210> SEQ ID NO 39
<211> LENGTH: 22
<212> TYPE: DNA
<213> ORGANISM: Artificial Sequence
<220> FEATURE:
<223> OTHER INFORMATION: Synthetic

<400> SEQUENCE: 39
ccgctagact aatgtgatta cc                                                 22

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
gagggataat tggattcccc g                                                  21

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
gagggataat tggattaccc g                                                  21
```